(12) United States Patent
Shan

(10) Patent No.: US 9,420,987 B2
(45) Date of Patent: Aug. 23, 2016

(54) STETHOSCOPE HEAD

(71) Applicant: Wuxi Kaishun Medical Device Manufacturing Co., Ltd., Wuxi, Jiangsu (CN)

(72) Inventor: Xijie Shan, Jiangsu (CN)

(73) Assignee: Wuxi Kaishun Medical Device Manufacturing Co., Ltd. (CN)

( * ) Notice: Subject to any disclaimer, the term of this patent is extended or adjusted under 35 U.S.C. 154(b) by 0 days.

(21) Appl. No.: 14/400,976

(22) PCT Filed: Apr. 26, 2013

(86) PCT No.: PCT/CN2013/074794
§ 371 (c)(1),
(2) Date: Nov. 13, 2014

(87) PCT Pub. No.: WO2013/170696
PCT Pub. Date: Nov. 21, 2013

(65) Prior Publication Data
US 2015/0164465 A1  Jun. 18, 2015

(30) Foreign Application Priority Data

May 15, 2012 (CN) .......................... 2012 1 0148071
May 15, 2012 (CN) ...................... 2012 2 0214856 U

(51) Int. Cl.
*A61B 7/02* (2006.01)
*G10K 11/08* (2006.01)
*G10K 11/22* (2006.01)

(52) U.S. Cl.
CPC . *A61B 7/02* (2013.01); *G10K 11/08* (2013.01); *G10K 11/22* (2013.01)

(58) Field of Classification Search
CPC ........... A61B 7/02; A61B 7/026; G10K 11/08
USPC ........................................................ 181/131
See application file for complete search history.

(56) References Cited

U.S. PATENT DOCUMENTS 3,515,239 A * 6/1970 Littmann ............... A61B 7/026
                                                                    181/137
4,502,562 A * 3/1985 Nelson ................... A61B 7/026
                                                                    181/131

(Continued)

FOREIGN PATENT DOCUMENTS

CN          2582541 Y       10/2003
CN        101411624 A        4/2009

(Continued)

OTHER PUBLICATIONS

Translation of EP 0284946 A1; accessed Oct. 8, 2015; <http://translationportal.epo.org/emtp/translate/?Action=description-retrieval&COUNTRY=EP&ENGINE=google&FORMAT=docdb&KIND=A1&LOCALE=en_EP&NUMBER=0284946&OPS=ops.epo.org/3.1&SRCLANG=de&TRGLANG=en>.*

*Primary Examiner* — Jeremy Luks
(74) *Attorney, Agent, or Firm* — Terrence J. Edwards; TechLaw Ventures, PLLC

(57) ABSTRACT

A detection head of a stethoscope comprises a detection head body (1, 2, 8) and a sound guiding conduit in the detection head body (1, 2). The sound guiding conduit comprises a sound collecting surface (12, 23), a sound guiding pore (D), and a lateral sound guiding aperture (4). The sound collecting surface (12, 23), the sound guiding pore (D), and the lateral sound guiding aperture (4) are disposed on the detection head body (1, 2, 8), and in combination with each other. At least a part of the detection head body (1, 2, 8) is made of a second density material. The density of the material of a sound guiding layer (3, 5, 6, 7, 9A) on the sound collecting surface (12, 23) is greater than that of the second density material.

14 Claims, 7 Drawing Sheets

(56) References Cited

U.S. PATENT DOCUMENTS

| | | | | |
|---|---|---|---|---|
| 4,770,270 A | * | 9/1988 | Grimm | A61B 7/026 181/131 |
| 5,616,890 A | * | 4/1997 | Boussignac | A61B 7/026 181/131 |
| 5,910,992 A | | 6/1999 | Ho | |
| 5,945,640 A | * | 8/1999 | Rossini | A61B 7/026 181/131 |
| 6,308,798 B1 | * | 10/2001 | Rashman | A61B 7/026 181/131 |
| 6,847,720 B2 | * | 1/2005 | Tseng | G09F 23/00 181/131 |
| 7,721,843 B1 | * | 5/2010 | Belenger | A61B 7/02 181/131 |
| 2006/0283656 A1 | * | 12/2006 | Lin | A61B 7/02 181/131 |

FOREIGN PATENT DOCUMENTS

| | | |
|---|---|---|
| CN | 201481445 U | 5/2010 |
| CN | 102670239 A | 9/2012 |
| CN | 202526206 U | 11/2012 |
| EP | 0284946 A1 | 10/1988 |

* cited by examiner

STETHOSCOPE HEAD

CROSS-REFERENCES TO RELATED APPLICATIONS

This application is a United States national phase application of co-pending international patent application number PCT/CN2013/074794, filed Apr. 26, 2013, which claims priority to Chinese patent application number 201220214856.5, filed May 15, 2012, and Chinese patent application number 201210148071.7, filed May 15, 2012, the disclosures of which are incorporated herein by reference.

TECHNICAL FIELD

The present disclosure relates to a medical instrument accessory, in particular to an accessory of a stethoscope, and more particularly to a stethoscope head.

TECHNICAL BACKGROUND

High density materials such as copper (with a density of 8.9 g/cm$^3$), titanium alloy (with a density of 7.82 g/cm$^3$), steel or particularly stainless steel (with a density of 7.8 g/cm$^3$), and zinc alloy (with a density of 6.58 g/cm$^3$) can conduct sounds with a fast speed and low attenuation, and the conducted sounds can be clearly heard, thus a stethoscope head in the prior art is typically made of the high density materials. However, the high density materials are expensive in price, heavy in weight, and monotonous in color, therefore, the stethoscope head is inconvenient in use.

Further, considering that the stethoscope head is generally made of the high density materials such as titanium alloy, copper and stainless steel, cutting tools used for machining such stethoscope head have a very high cost and the time taken for the machining is long, thus the stethoscope head is costly, thereby greatly increasing consumer costs.

Furthermore, the stethoscope head in the prior art is formed integrally and has a shape similar to a waist drum, that is, both ends of the stethoscope head are larger than the middle part of the stethoscope head, and a mold cannot be stripped in mold casting the stethoscope head, thus the stethoscope head can only be made by a milling process at a low working efficiency.

SUMMARY OF THE INVENTION

The present invention provides a stethoscope head which is light in weight, low in cost and does not affect the listening experience.

The present invention further provides a method for reducing a weight of a stethoscope head.

The present invention is realized as below.

A stethoscope head, where the stethoscope head includes a head body and a sound guiding conduit formed in the head body, the sound guiding conduit includes a sound collecting surface, a sound guiding pore and a lateral sound guiding aperture, all of which are located on the head body and intercommunicated with each other, at least a portion of the head body is made of a second density material, a density of a sound guiding layer on the sound collecting surface is larger than that of the second density material.

Further, a density of a sound guiding layer in the sound guiding pore is larger than that of the second density material, also, the density of the sound guiding layer in the sound guiding pore is the same as or different from that of a sound guiding layer on the sound collecting surface.

Furthermore, the head body is separated and includes an upper head body and a lower head body which are mutually fitted with each other, the sound collecting surface includes an upper sound collecting surface disposed on the upper head body and a lower sound collecting surface disposed on the lower head body, the upper sound collecting surface is communicated with the lower sound collecting surface through the sound guiding pore, the sound guiding pore is communicated with the lateral sound guiding aperture, the lower head body is made of the same material as or different material from that of the upper head body, but at least one of the lower head body and the upper head body is made of the second density material.

If the head body consists of an upper head body and a lower head body which are fitted with each other and a density of the lower head body is different from that of the upper head body, there are three situations are further illustrated as below.

First, if the upper head body is made of a first density material, the lower head body is made of a second density material, a density of the first density material is larger than that of the second density material.

A stethoscope head includes a head body and a sound guiding conduit formed in the head body, the sound guiding conduit includes a sound collecting surface, a sound guiding pore and a lateral sound guiding aperture, all of which are located on the head body and intercommunicated with each other, the head body is separated and includes an upper head body and a lower head body, which are mutually fitted with each other.

The sound collecting surface includes an upper sound collecting surface disposed on the upper head body and a lower sound collecting surface disposed on the lower head body, the upper sound collecting surface is communicated with the lower sound collecting surface through the sound guiding pore, the sound guiding pore intersects with and communicates with the lateral sound guiding aperture.

A tubular rivet is disposed at and fitted with one end of the sound guiding pore of the lower head body by an interference fit, a tolerance fit or a screw thread fit. A rod chamber of the tubular rivet runs through two ends of the tubular rive along an axis of the tubular rivet. A cap portion surface of the tubular rivet is shape-matching with one end surface of the lower head body. The end of the rod portion of the tubular rivet abuts against the lateral sound guiding aperture.

A profiled tubular rivet is disposed at and is fitted with the other end of the sound guiding pore in the lower head body by an interference fit, a tolerance fit or a screw thread fit. An outside surface of a head portion of the profiled tubular rivet is shape-matching with the lower collecting surface of the lower head body. A rod chamber of the tubular rivet runs through two ends of the tubular rivet along an axis of the tubular rivet. An end of the rod portion of the profiled tubular rivet abuts against the lateral sound guiding aperture.

A stethoscope head includes a head body and a sound guiding conduit formed in the head body, the sound guiding conduit includes a sound collecting surface, a sound guiding pore and a lateral sound guiding aperture, all of which are located on the head body and intercommunicated with each other, the head body is separated and includes an upper head body and a lower head body, which are mutually fitted with each other.

The sound collecting surface includes an upper sound collecting surface disposed on the upper head body and a lower sound collecting surface disposed on the lower head body, the upper sound collecting surface is communicated with the lower sound collecting surface through the sound guiding pore, the sound guiding pore intersects with and communicates with the lateral sound guiding aperture.

A tubular rivet is disposed at and fitted with one end of the sound guiding pore of the lower head body by an interference fit, a tolerance fit or a screw thread fit. A rod chamber of the tubular rivet runs through two ends of the tubular rive along an axis of the tubular rivet. A cap portion surface of the tubular rivet is shape-matching with and closely fitted with one end surface of the lower head body. A hole is formed in a rod portion of the tubular rivet and runs through the two side tube walls of the rod portion, an axis of the hole overlaps with that of the lateral sound guiding aperture, and an aperture of the hole is the same as that of the that of the lateral sound guiding aperture.

A profiled tubular rivet is disposed at and fitted with the other end of the sound guiding pore of the lower head body by an interference fit, a tolerance fit or a screw thread fit. An outside surface of a head portion of the profiled tubular rivet is shape-matching with the lower sound collecting surface of the lower head body. A rod chamber of the profiled tubular rivet runs through two ends of the profiled tubular rivet along an axis thereof. An end of the rod portion of the profiled tubular rivet abuts against the tubular rivet.

A stethoscope head includes a head body and a sound guiding conduit formed in the head body, the sound guiding conduit includes a sound collecting surface, a sound guiding pore and a lateral sound guiding aperture, all of which are located on the head body and intercommunicated with each other, the head body is separated and includes an upper head body and a lower head body, which are mutually fitted with each other.

The sound collecting surface includes an upper sound collecting surface disposed on the upper head body and a lower sound collecting surface disposed on the lower head body, the upper sound collecting surface is communicated with the lower sound collecting surface through the sound guiding pore, the sound guiding pore intersects with and communicates with the lateral sound guiding aperture.

A tubular rivet is disposed at and fitted with one end of the sound guiding pore of the lower head body by an interference fit, a tolerance fit or a screw thread fit. A rod chamber of the tubular rivet runs through two ends of the tubular rive along an axis of the tubular rivet. A cap portion surface of the tubular rivet is shape-matching with and closely fitted with one end surface of the lower head body.

A profiled tubular rivet is disposed at and fitted with the other end of the sound guiding pore of the lower head body by an interference fit, a tolerance fit or a screw thread fit. An outside surface of a head portion of the profiled tubular rivet is shape-matching with the lower sound collecting surface of the lower head body. A rod chamber of the profiled tubular rivet runs through two ends of the profiled tubular rivet along an axis thereof. A hole is formed in a rod portion of the profiled tubular rivet and runs through the two side tube walls of the rod portion, an axis of the hole overlaps with that of the lateral sound guiding aperture, and an aperture of the hole is the same as that of the that of the lateral sound guiding aperture. A rod portion of the profiled tubular rivet abuts against the rod portion of the tubular rivet.

A stethoscope head includes a head body and a sound guiding conduit formed in the head body, the sound guiding conduit includes a sound collecting surface, a sound guiding pore and a lateral sound guiding aperture, all of which are located on the head body and intercommunicated with each other, the head body is separated and includes an upper head body and a lower head body, which are mutually fitted with each other.

A hollow tube is disposed in and fitted with the sound guiding pore of the lower head body.

A tubular rivet is disposed at and fitted with one end of the sound guiding pore of the lower head body by an interference fit, a tolerance fit or a screw thread fit. A rod chamber of the tubular rivet runs through two ends of the tubular rive along an axis thereof. A cap portion surface of the tubular rivet is shape-matching with and closely fitted with one end surface of the lower head body. An end of the rod portion of the tubular rivet abuts against one end of the hollow tube.

A profiled tubular rivet is disposed at and fitted with the other end of the sound guiding pore of the lower head body by an interference fit, a tolerance fit or a screw thread fit. An outside surface of a head portion of the profiled tubular rivet is shape-matching with the lower sound collecting surface of the lower head body. A rod chamber of the profiled tubular rivet runs through two ends of the profiled tubular rivet along an axis thereof. An end of the rod portion of the profiled tubular rivet abuts against the other end of the hollow tube.

The lateral sound guiding aperture is communicated with a tube chamber of the hollow tube, a rod chamber of the tubular rivet, a rod chamber of the profiled tubular rivet.

Further, a hole is formed in the hollow tube, communicated with the side guiding hole and runs through at least one side tube wall of the lateral sound guiding aperture.

A stethoscope head includes a head body and a sound guiding conduit formed in the head body, the sound guiding conduit includes a sound collecting surface, a sound guiding pore and a lateral sound guiding aperture, all of which are located on the head body and intercommunicated with each other, the head body is separated and includes an upper head body and a lower head body, which are mutually fitted with each other.

A hollow tube is disposed in and fitted with the sound guiding pore of the lower head body.

A tubular rivet is disposed at and fitted with one end of the sound guiding pore of the lower head body by an interference fit, a tolerance fit or a screw thread fit. A rod chamber of the tubular rivet runs through two ends of the tubular rive along an axis thereof. A cap portion surface of the tubular rivet is shape-matching with and closely fitted with one end surface of the lower head body. An end of the rod portion of the tubular rivet abuts against one end of the hollow tube.

A profiled tubular rivet is disposed at and fitted with the other end of the sound guiding pore of the lower head body by an interference fit, a tolerance fit or a screw thread fit. An outside surface of a head portion of the profiled tubular rivet is shape-matching with the lower sound collecting surface of the lower head body. A rod chamber of the profiled tubular rivet runs through two ends of the profiled tubular rivet along an axis thereof. An end of the rod portion of the profiled tubular rivet abuts against the other end of the hollow tube.

The lateral sound guiding aperture is communicated with a tube chamber of the hollow tube, a rod chamber of the tubular rivet, a rod chamber of the profiled tubular rivet.

Further, a hole is formed in a rod portion of the semi-tubular, the hole communicates with the lateral sound guiding aperture and runs through at least one side tube wall of the lateral sound guiding aperture.

A stethoscope head, where the stethoscope head includes a head body and a sound guiding conduit formed in the head body, the sound guiding conduit includes a sound collecting surface, a sound guiding pore and a lateral sound guiding aperture, all of which are located on the head body, the stethoscope head is separated and includes an upper head body and a lower head body which are mutually fitted with each other.

A hollow tube is disposed in and fitted with the sound guiding pore of the lower head body.

A tubular rivet is disposed at and fitted with one end of the sound guiding pore of the lower head body by an interference fit, a tolerance fit or a screw thread fit. A rod chamber of the tubular rivet runs through two ends of the tubular rive along an axis thereof. A cap portion surface of the tubular rivet is shape-matching with and closely fitted with one end surface of the lower head body. An end of the rod portion of the tubular rivet abuts against one end of the hollow tube.

A profiled tubular rivet is disposed at and fitted with the other end of the sound guiding pore of the lower head body by an interference fit, a tolerance fit or a screw thread fit. An outside surface of a head portion of the profiled tubular rivet is shape-matching with the lower sound collecting surface of the lower head body. A rod chamber of the profiled tubular rivet runs through two ends of the profiled tubular rivet along an axis thereof. An end of the rod portion of the profiled tubular rivet abuts against the other end of the hollow tube.

The lateral sound guiding aperture is communicated with a tube chamber of the hollow tube, a rod chamber of the tubular rivet, a rod chamber of the profiled tubular rivet.

Further, a hole is formed in the profiled tubular rivet and runs through at least one side tube wall of the lateral sound guiding aperture, an axis of the hole overlaps with that of the lateral sound guiding aperture, and an aperture of the hole is the same as that of the that of the lateral sound guiding aperture Second, if the lower head body is made of a first density material, the upper head body is made of a second density material, a density of the first density material is larger than that of the second density material.

A stethoscope head includes a head body and a sound guiding conduit formed in the head body, the sound guiding conduit includes a sound collecting surface, a sound guiding pore and a lateral sound guiding aperture, all of which are located on the head body, the head body is separated and includes an upper head body and a lower head body, which are mutually fitted with each other.

The sound collecting surface includes an upper sound collecting surface disposed on the upper head body and a lower sound collecting surface disposed on the lower head body, the upper sound collecting surface is communicated with the lower sound collecting surface through the sound guiding pore, the sound guiding pore intersects with and communicates with the lateral sound guiding aperture.

A profiled tubular rivet is disposed at and fitted with one end of the sound guiding pore of the upper head body by an interference fit, a tolerance fit or a screw thread fit. An outside surface of a head portion of the profiled tubular rivet is shape-matching with the upper sound collecting surface of the upper head body. A rod chamber of the profiled tubular rivet runs through two ends of the profiled tubular rivet along an axis thereof. The other end of the sound guiding pore in the upper head body is provided with an internal thread which is fitted with the lower head body. An outside surface of one end of the lower head body is provided with an external thread which is fitted with the internal thread.

Third, if both of the lower head body and the upper head body are made of the second density material.

A stethoscope head includes a head body and a sound guiding conduit formed in the head body, the sound guiding conduit includes a sound collecting surface, a sound guiding pore and a lateral sound guiding aperture, all of which are located on the head body, the head body is separated and includes an upper head body and a lower head body, which are mutually fitted with each other.

The sound collecting surface includes an upper sound collecting surface disposed on the upper head body and a lower sound collecting surface disposed on the lower head body, the upper sound collecting surface is communicated with the lower sound collecting surface through the sound guiding pore, the sound guiding pore intersects with and communicates with the lateral sound guiding aperture.

A first profiled tubular rivet is disposed at and fitted with the one end of the sound guiding pore of the upper head body by an interference fit, a tolerance fit or a screw thread fit. An outside surface of a head portion of the first profiled tubular rivet is shape-matching with the upper sound collecting surface of the upper head body. A rod chamber of the first profiled tubular rivet runs through two ends of the first profiled tubular rivet along an axis thereof. The other end of the sound guiding pore of the upper head body is provided with an internal thread which is fitted with the lower head body.

A tubular rivet is disposed at and fitted with one end of the sound guiding pore of the lower head body by an interference fit. A rod chamber of the tubular rivet runs through two ends of the tubular rive along an axis thereof. A cap portion surface of the tubular rivet is shape-matching with and closely fitted with one end surface of the lower head body. An end of the rod portion of the tubular rivet abuts against the lateral sound guiding aperture.

A second profiled tubular rivet is disposed at and fitted with the other end of the sound guiding pore of the lower head body by an interference fit. An outside surface of a head portion of the second profiled tubular rivet is shape-matching with the lower sound collecting surface. A chamber in the rod portion of the second profiled tubular rivet runs through both ends of the second profiled tubular rivet along an axis thereof. An end of the rod portion of the second profiled tubular rivet abuts against the lateral sound guiding aperture.

An outside surface of one end of the lower head body is provided with an external thread which is fitted with the internal thread.

A stethoscope head includes a head body and a sound guiding conduit formed in the head body, the sound guiding conduit includes a sound collecting surface, a sound guiding pore and a lateral sound guiding aperture, all of which are located on the head body, the head body is separated and includes an upper head body and a lower head body, which are mutually fitted with each other.

The sound collecting surface includes an upper sound collecting surface disposed on the upper head body and a lower sound collecting surface disposed on the lower head body, the upper sound collecting surface is communicated with the lower sound collecting surface through the sound guiding pore, the sound guiding pore intersects with and communicates with the lateral sound guiding aperture.

A first profiled tubular rivet is disposed at and fitted with the one end of the sound guiding pore of the upper head body by an interference fit, a tolerance fit or a screw thread fit. An outside surface of a head portion of the first profiled tubular rivet is shape-matching with the upper sound collecting surface of the upper head body. A rod chamber of the first profiled tubular rivet runs through two ends of the first profiled tubular rivet along an axis thereof. The other end of the sound guiding pore of the upper head body is provided with an internal thread which is fitted with the lower head body.

A tubular rivet is disposed at and fitted with one end of the sound guiding pore of the lower head body by an interference fit, a tolerance fit or a screw thread fit, a rod chamber of the tubular rivet runs through two ends of the tubular rive along an axis thereof, a cap portion surface of the tubular rivet is shape-matching with and closely fitted with one end surface of the lower head body; a hole is formed in the rod portion of the tubular rivet, the hole runs through the two side tube walls of the rod portion, an axis of the hole overlaps with that of the lateral sound guiding aperture, and an aperture of the hole is the same as that of the that of the lateral sound guiding aperture.

A second profiled tubular rivet is disposed at and fitted with the other end of the sound guiding pore of the lower head body by an interference fit, an outside surface of a head portion of the second profiled tubular rivet is shape-matching with the lower sound collecting surface, a chamber in the rod portion of the second profiled tubular rivet runs through both ends of the second profiled tubular rivet along an axis thereof, an end of the rod portion of the second profiled tubular rivet abuts against that of the tubular rivet.

An outside surface of one end of the lower head body is provided with an external thread which is fitted with the internal thread.

A stethoscope head includes a head body and a sound guiding conduit formed in the head body, the sound guiding conduit includes a sound collecting surface, a sound guiding pore and a lateral sound guiding aperture, all of which are located on the head body, the head body is separated and includes an upper head body and a lower head body, which are mutually fitted with each other.

The sound collecting surface includes an upper sound collecting surface disposed on the upper head body and a lower sound collecting surface disposed on the lower head body, the upper sound collecting surface is communicated with the lower sound collecting surface through the sound guiding pore, the sound guiding pore intersects with and communicates with the lateral sound guiding aperture.

A first profiled tubular rivet is disposed at and fitted with the one end of the sound guiding pore of the upper head body by an interference fit, a tolerance fit or a screw thread fit. An outside surface of a head portion of the first profiled tubular rivet is shape-matching with the upper sound collecting surface of the upper head body. A rod chamber of the first profiled tubular rivet runs through two ends of the first profiled tubular rivet along an axis thereof. The other end of the sound guiding pore of the upper head body is provided with an internal thread which is fitted with the lower head body.

A tubular rivet is disposed at and fitted with one end of the sound guiding pore of the lower head body by an interference fit. A rod chamber of the tubular rivet runs through two ends of the tubular rive along an axis thereof. A cap portion surface of the tubular rivet is shape-matching with and closely fitted with one end surface of the lower head body. A second profiled tubular rivet is disposed at and fitted with the other end of the sound guiding pore of the lower head body by an interference fit. An outside surface of a head portion of the second profiled tubular rivet is shape-matching with the lower sound collecting surface. A chamber in the rod portion of the second profiled tubular rivet runs through both ends of the second profiled tubular rivet along an axis thereof. A rod portion of the second profiled tubular rivet abuts against that of the lateral sound guiding aperture.

An outside surface of one end of the lower head body is provided with an external thread which is fitted with the internal thread.

Where, the sound collecting surface may be a curved surface, a conical surface or a combination thereof.

If the head body is integrated:

A stethoscope head includes a head body and a sound guiding conduit formed in the head body, the sound guiding conduit includes a sound collecting surface, a sound guiding pore and a lateral sound guiding aperture, all of which are located on the head body and intercommunicated with each other; the head body is integrated and made of a second density material, the sound collecting surface may include only one sound collecting surface, a sound guiding layer is the same as the sound collecting surface in shape and includes a hole which runs through a bottom thereof and is communicated with the sound guiding pore, the sound guiding layer consists of a profiled tubular rivet, a density of the profiled tubular rivet is larger than that of the second density material.

Further, an outside surface of the profiled tubular rivet is shape-matching with and closely fitted with the sound collecting surface of the head body, an outside surface of a rod portion of the profiled tubular rivet is closely fitted with the sound guiding pore. A rod portion of the profiled tubular rivet is fitted with the sound guiding pore by an interference fit, a tolerance fit or a screw thread fit.

Further, a rod chamber of the profiled tubular rivet is communicated with the lateral sound guiding aperture.

Further, the sound collecting surface may include an upper sound collecting surface and a lower sound collecting surface; the profiled tubular rivet includes a first profiled tubular rivet and a third profiled tubular rivet.

A rod chamber of the first profiled tubular rivet runs through two ends of the first profiled tubular rivet. A rod chamber of the third profiled tubular rivet runs through two ends of the third profiled tubular rivet.

An outside surface of a head portion of the first profiled tubular rivet is shape-matching with and closely fitted with the upper sound collecting surface, an outside surface of a rod portion of the first profiled tubular rivet is closely fitted with the sound guiding pore, a rod chamber of the first profiled tubular rivet is communicated with the lateral sound guiding aperture.

An outside surface of a head portion of the third profiled tubular rivet is shape-matching with and closely fitted with the upper sound collecting surface, an outside surface of a rod portion of the third profiled tubular rivet is closely fitted with the sound guiding pore, a rod chamber of the third profiled tubular rivet is communicated with the lateral sound guiding aperture.

Further, the sound collecting surface may include an upper sound collecting surface and a lower sound collecting surface; the profiled tubular rivet includes a first profiled tubular rivet and a third profiled tubular rivet.

A rod chamber of the first profiled tubular rivet runs through two ends of the first profiled tubular rivet. A rod chamber of the third profiled tubular rivet runs through two ends of the third profiled tubular rivet.

An outside surface of a head portion of the first profiled tubular rivet is shape-matching with and closely fitted with the upper sound collecting surface, an outside surface of a rod portion of the first profiled tubular rivet is closely fitted with the sound guiding pore. A rod portion of the first profiled tubular rivet is fitted with the sound guiding pore by an interference fit, a tolerance fit or a screw thread fit. A rod chamber of the first profiled tubular rivet is communicated with the lateral sound guiding aperture.

An outside surface of a head portion of the third profiled tubular rivet is shape-matching with and closely fitted with the upper sound collecting surface, an outside surface of a rod portion of the third profiled tubular rivet is closely fitted with the sound guiding pore. A rod portion of the profiled tubular rivet is fitted with the sound guiding pore by an interference fit, a tolerance fit or a screw thread fit. A rod portion of the third profiled tubular rivet is fitted with the sound guiding pore by an interference fit, a tolerance fit or a screw thread fit, a rod chamber of the third profiled tubular rivet is communicated with the lateral sound guiding aperture. An end of the rod portion of the first profiled tubular rivet abuts against the third profiled tubular rivet.

A hole is formed in the rod portion of the first profiled tubular rivet or the third profiled tubular rivet, the hole is communicated with a rotation shaft and the rod chamber and runs through at least one side rod wall of the rod portion.

Further, the sound collecting surface may include an upper sound collecting surface and a lower sound collecting surface; the profiled tubular rivet includes a first profiled tubular rivet and a third profiled tubular rivet.

A rod chamber of the first profiled tubular rivet runs through two ends of the first profiled tubular rivet. A rod chamber of the third profiled tubular rivet runs through two ends of the third profiled tubular rivet.

An outside surface of a head portion of the first profiled tubular rivet is shape-matching with and closely fitted with the upper sound collecting surface, an outside surface of a rod portion of the first profiled tubular rivet is closely fitted with the sound guiding pore, a rod chamber of the first profiled tubular rivet is communicated with the lateral sound guiding aperture.

An outside surface of a head portion of the third profiled tubular rivet is shape-matching with and closely fitted with the upper sound collecting surface, an outside surface of a rod portion of the third profiled tubular rivet is closely fitted with the sound guiding pore, a rod chamber of the third profiled tubular rivet is communicated with the lateral sound guiding aperture.

A sound guiding layer on an inner wall of the sound guiding pore is a hollow tube. An outer wall of the hollow tube is closely fitted with the inner wall of the sound guiding pore. The hollow tube is fitted with the sound guiding pore by an interference fit, a tolerance fit or a screw thread fit. Two ends of the hollow tube abuts against an end of the rod portion of the first profiled tubular rivet and an end of the rod portion of the third profiled tubular rivet respectively.

A hole is formed in the hollow tube, the hole is communicated with the lateral sound guiding aperture and the rod chamber and runs through at least one side rod wall of the rod portion.

A stethoscope head includes a head body and a sound guiding conduit formed in the head body, the sound guiding conduit includes a sound collecting surface, a sound guiding pore and a lateral sound guiding aperture, all of which are located on the head body; the head body is integrated and made of a second density material, the sound guiding layer is composed of a profiled tubular rivet, a density of the profiled tubular rivet is larger than that of the second density material.

Further, an outside surface of a head portion of the profiled tubular rivet is shape-matching with and closely fitted with the sound collecting surface of the head body, a rod portion of the profiled tubular rivet is fitted with the sound guiding pore by an interference fit, a tolerance fit or a screw thread fit, an outside surface of a rod portion of the profiled tubular rivet is closely fitted with the sound guiding pore.

Further, a rod chamber of the profiled tubular rivet is communicated with the lateral sound guiding aperture.

Further, a sound guiding layer on an inner wall of the sound guiding pore may be a hollow tube. An outer wall of the hollow tube is fitted with the inner wall of the sound guiding pore in a non-ratable and immovable manner. Two ends of the hollow tube abut against rod ends of the profiled tubular rivet. A hole is formed in the hollow tube, an axis of the hole overlaps with that of the lateral sound guiding aperture, an aperture of the hole is the same as that of the that of the lateral sound guiding aperture, the hole runs through at least one side rod wall of the rod portion and is communicated with the rod chamber.

The present disclosure can be implemented in the following ways.

A method for reducing a weight of a stethoscope head, where the stethoscope head includes a head body and a sound guiding conduit formed in the head body, the which sound guiding conduit includes a sound collecting surface, a sound guiding pore and a lateral sound guiding aperture, all of which are located on the head body, a first density material is provided, at least the sound guiding layer on the sound collecting surface is made of the first density material so as to ensure a sound conducting quality of the stethoscope head; a second density material is provided, at least a portion of the stethoscope head is made of the second density material, a density of the second density material is less than that of the first density material.

Further, a sound guiding layer in the sound guiding pore is made of a third density material, the density of the second density material is less than that of the third density material, a density of the third density material is the same as or different from that of the first density material.

The densities of the various materials are as follows: such as copper (with a density of 8.9 g/cm$^3$), titanium alloy (with a density of 7.82 g/cm$^3$), stainless steel, steel (with a density of 7.8 g/cm$^3$), zinc alloy (with a density of 6.58 g/cm$^3$) or aluminium alloy (with a density of 2.7 g/cm$^3$), engineering plastics (with a density of in a range of 0.8 g/cm$^3$ to 2 g/cm$^3$) and engineering rubber (with a density of in a range of 0.4 g/cm$^3$ to 1.5 g/cm$^3$)

The present disclosure possesses the following benefits.

First, the head body is made of a low density material, thereby reducing a weight of the head body per se, second, the sound is reflected by the sound guiding layer during conducting of the sound and the sound guiding layer is made of a higher density material, therefore the conduction and magnification of the sound are improved, the hearing effect does not been affected, the present further possesses the following benefits.

First, a consumption of the high density material is reduced by 50%, the cost of the material is significantly reduced.

Second, a machining of the high density material is reduced by 40%, thereby reducing consumed cutting tools and machining time required for machining the high density material, the cost for machining is significantly reduced, for example, a machining manner in which the high density material is enclosed by the low density material by an injection is high in efficiency and low in cost.

Third, a weight of the head body is reduced to 60%, thereby the product is portable.

Fourth, a color of the stethoscope head are enriched, thereby providing various color match, for example, the two different densities materials may select from different colors.

The upper head body and lower head body are formed by casting because the head body is separated, thereby greatly reducing the processing difficulty for vehicle processing in the prior art and a cost for working.

1: upper head body; 11: internal thread; 12: upper sound collecting surface; 2: lower head body; 21: end surface; 22: external thread; 23: lower sound collecting surface; 3: tubular rivet; 31: chamber in a rod portion; 32: cap portion of the tubular rivet; 33: end of the rod portion of the tubular rivet; 34: hole; 35: rod portion; 4: lateral sound guiding aperture; D: sound guiding pore; 5: first profiled tubular rivet; 51: outside surface of a head portion; 52: chamber in a rod portion; 53: end of the rod portion; 54: hole; 55: rod portion; 5A: profiled tubular rivet; 51A: outside surface of a head portion; 52A: chamber in a rod portion; 53A: end of a rod portion of a first profiled tubular rivet; 54A: hole; 55A: rod portion; 57A: nailhead; 6: second profiled tubular rivet 61: outside surface of a head portion; 62: chamber in the rod portion; 63: rod portion; 7: third profiled tubular rivet; 71: outside surface of a head portion; 72: chamber in the rod portion; 73: rod portion; 74: end of the rod portion; 8: head body; 9: hollow tube; 91: tube chamber; 92: inner wall 93: hole; 93A: hollow tube; 92A: inner wall; 93A: hole.

DETAILED DESCRIPTION OF THE EMBODIMENTS

In order to illustrate the present disclosure and the beneficial effects thereof in detail, the present disclosure will be further illustrated below with reference to the accompanying drawings, and the protection scope of the present disclosure is not limited to the contents of the specific embodiments.

The present disclosure is further illustrated with reference to the drawings.

Figure 1:
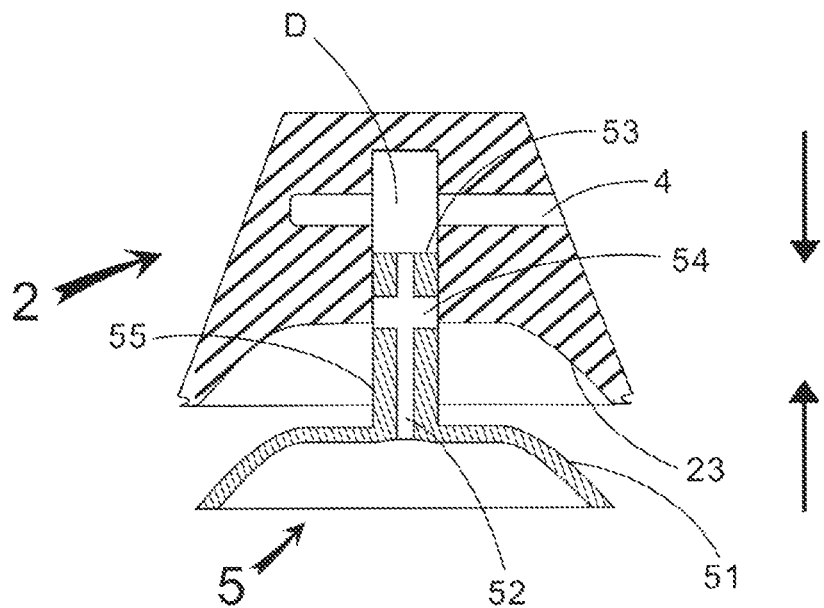
FIG. 1 is a schematic diagram the present disclosure (with one sound collecting surface)
Figure 2:
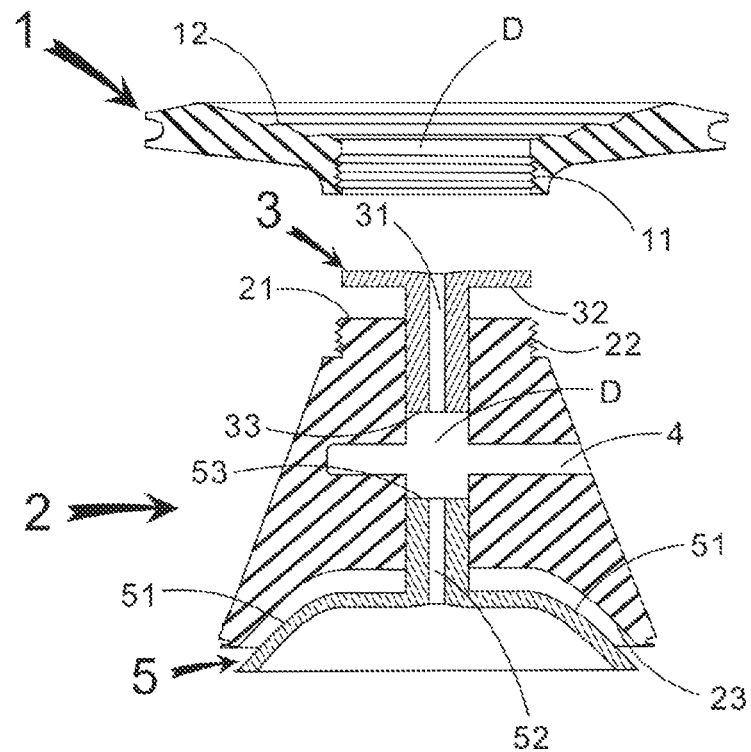
FIG. 2 is a schematic diagram showing an assembly of the present disclosure (where only a lower head body is made of a low-density material)
Figure 3:
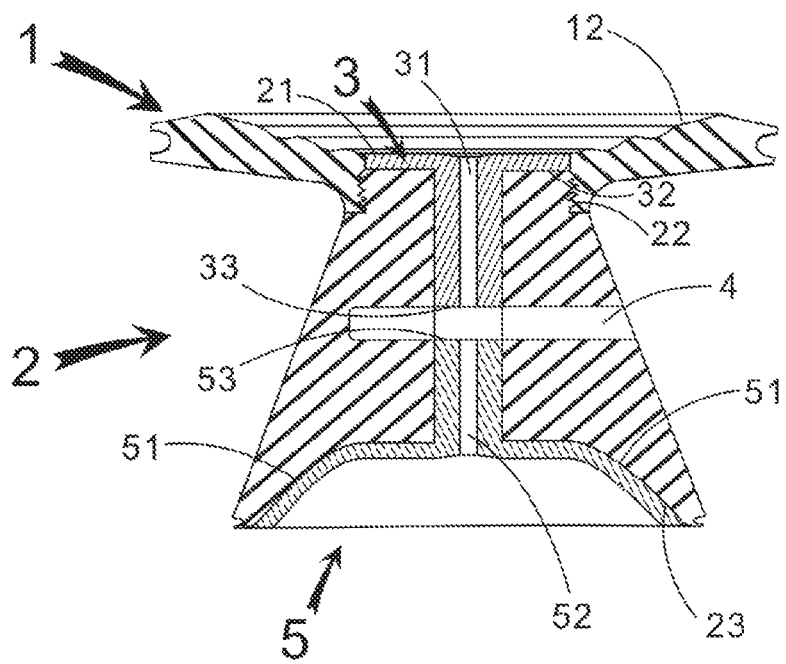
FIG. 3 is a schematic diagram showing the present disclosure (where only a lower head body is made of a low-density material)
Figure 4:
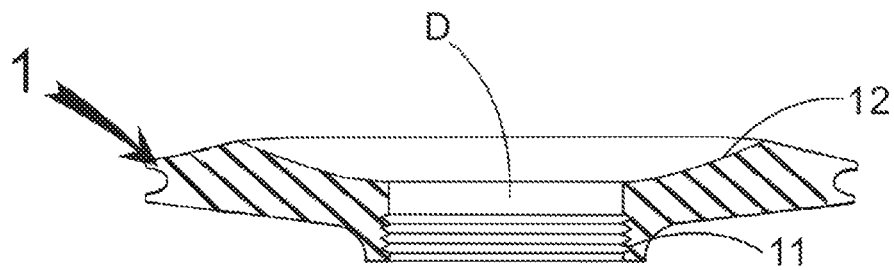
FIG. 4 is a schematic diagram showing an upper head body of the present disclosure.
Figure 5:
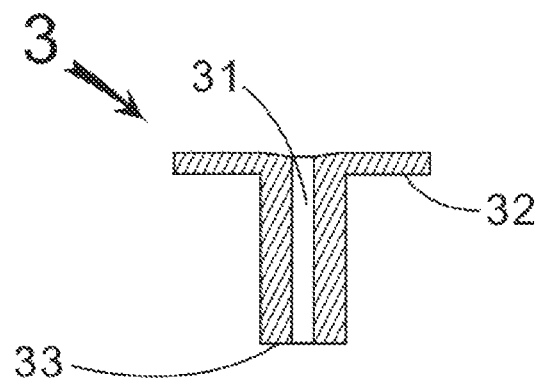
FIG. 5 is a schematic diagram showing a tubular rivet of the present disclosure.
Figure 6:
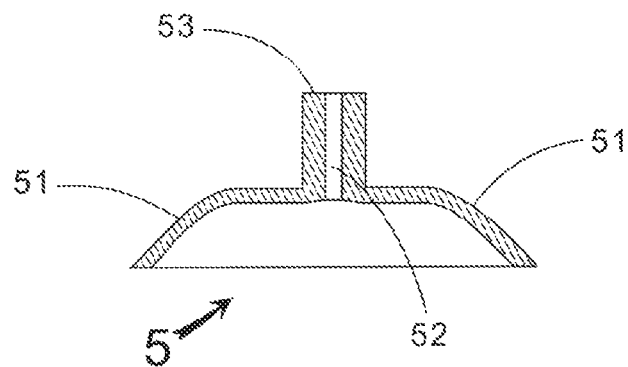
FIG. 6 is a schematic diagram showing a profiled tubular rivet of the present disclosure.
Figure 7:
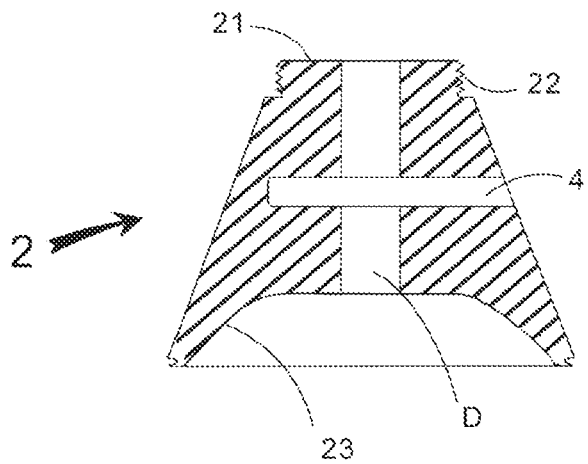
FIG. 7 is a schematic diagram showing a lower head body of the present disclosure.

In a first embodiment, the present disclosure is further illustrated below with reference to FIG. 1.

A stethoscope head includes a head body and a sound guiding conduit in the head body. The sound guiding conduit includes a lower sound collecting surface 23, a sound guiding pore D and a lateral sound guiding aperture 4. The lower sound collecting surface 23, the sound guiding pore D and the lateral sound guiding aperture 4 are provided in a lower head body 2.

In the present embodiment, there exists only one sound collecting surface, i.e. the lower sound collecting surface 23 in the present embodiment. A sound guiding layer is closely fitted on the lower sound collecting surface 23. The sound guiding layer may be a first profiled tubular rivet 5, an outside surface 51 of a head portion of the first profiled tubular rivet 5 fits the lower sound collecting surface 23 and closely matches with the lower sound collecting surface 23, and an outer surface of a rod portion 55 of the first profiled tubular rivet 5 closely matches with the sound guiding pore D.

A chamber 52 in the rod portion of the first profiled tubular rivet 5 runs through both ends of the first profiled tubular rivet 5. The chamber 52 is communicated with the lateral sound guiding aperture 4.

The rod portion 55 of the first profiled tubular rivet 5 includes a hole 54 which opens at a side wall of the rod portion 55 and is communicated with the chamber 52. The hole 54 is communicated with the lateral sound guiding aperture 4.

During machining, the lower head body 2 is formed by casing, subsequently the sound guiding pore D and the lateral sound guiding aperture 4 are formed in the lower head body 2, and then the rod portion 55 of the first profiled tubular rivet 5 is disposed in the sound guiding pore D.

Alternatively, the first profiled tubular rivet 5 is prepared, then the rod portion 55 and the outer end surface 51 of the first profiled tubular rivet 5 are covered by the lower head body 2 in a non-rotatable and immovable manner by injection moulding, thereby forming an integrated structure where the first profiled tubular rivet 5 is closely fitted with the lower head body 2.

Figure 17:
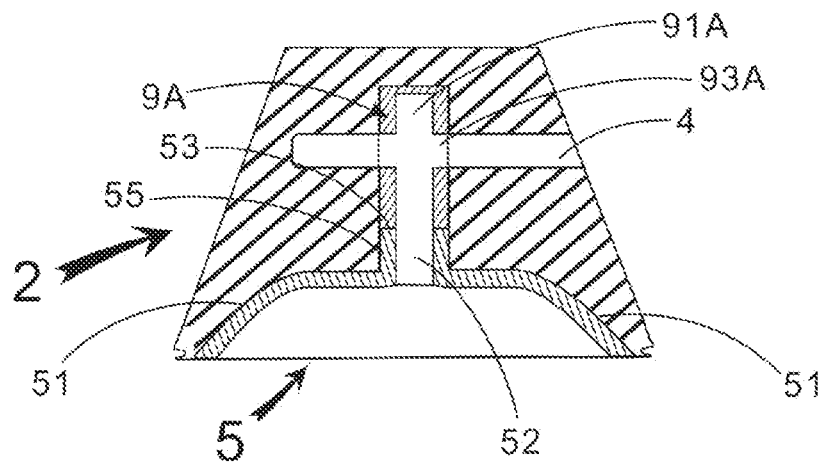
FIG. 17 is a schematic diagram of the present disclosure (where a head body is integrated).
Figure 18:
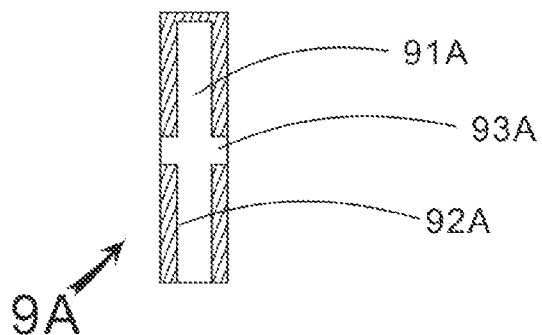
FIG. 18 is a schematic diagram showing a hollow tube of the present disclosure.

In a second embodiment, the present disclosure is further illustrated with reference to FIG. 17 and FIG. 18.

A stethoscope head includes a head body and a sound guiding conduit in the head body. The sound guiding conduit includes a lower sound collecting surface 23, a sound guiding pore D and a lateral sound guiding aperture 4. The lower sound collecting surface 23, the sound guiding pore D and the lateral sound guiding aperture 4 are provided in a lower head body 2.

A sound guiding layer is closely fitted on the lower sound collecting surface 23. The sound guiding layer may be a first profiled tubular rivet 5, an outside surface 51 of a head portion of the first profiled tubular rivet 5 fits the lower sound collecting surface 23 and closely matches with the lower sound collecting surface 23, and an outer surface of a rod portion 55 of the first profiled tubular rivet 5 closely matches with the sound guiding pore D.

A chamber 52 in the rod portion of the first profiled tubular rivet 5 runs through both ends of the first profiled tubular rivet 5. The chamber 52 is communicated with the lateral sound guiding aperture 4.

Further, a sound guiding layer made of aluminium alloy, which may be a hollow tube 9A with one blind end, is disposed on an inner wall of the sound guiding pore D. An outer wall of the hollow tube is closely fitted with an inner wall of the sound guiding pore D by means of tolerance fit, thread fit and so on.

An end 53 of the rod portion of the first profiled tubular rivet 5 is adjacent to but not in contact with an open end of the hollow tube 9A, alternatively, the end 53 of the rod portion of the first profiled tubular rivet 5 abuts against the open end of the hollow tube 9A.

The first profiled tubular rivet 5 and the hollow tube 9A may be made of steel especially stainless steel, copper, aluminium alloy or the like, and the lower head body 2 may be made of engineering plastics, engineering rubber or the like.

In a third embodiment, the present disclosure is further illustrated with reference to FIG. 2, FIG. 3, FIG. 4, FIG. 5, FIG. 6 and FIG. 7.

A stethoscope head consists of individual upper head body 1 and lower head body 2, an upper sound collecting surface 12 located on the upper head body 1, a lower sound collecting surface 23 which is located on the lower head body 2 and is opposite to the upper sound collecting surface 12, a lateral sound guiding aperture 4 in the lower head body 2, a tubular rivet 3 and a first profiled tubular rivet 5.

The upper head body 1 is provided with an internal thread 11, and the lower head body 2 is provided with an external thread 22, so that the upper head body 1 and the lower head body 2 are fixed together through the cooperation between the internal thread 11 and the external thread 22.

A sound guiding pore D runs through the upper head body 1 and the lower head body 2, so that the upper sound collecting surface 12 is communicated with the lower sound collecting surface 23 through the sound guiding pore D. The sound guiding pore D is communicated with and intersects with the lateral sound guiding aperture 4. The upper head body 1 is made of stainless steel, and the lower head body 2 is made of engineering plastics. The tubular rivet 3 is disposed at one end of the sound guiding pore D in the lower head body 2 by an interference fit. A rod chamber 31 (i.e. a chamber in a rod portion) of the tubular rivet 3 runs through two ends of the tubular rivet 3 along an axis of the tubular rivet 3. A cap portion 32 of the tubular rivet 3 is closely shape-fitted with an end surface 21 of the lower head body 2. A rod portion of the tubular rivet 3 is closely fitted with the sound guiding pore D. An end 33 of the rod portion of the tubular rivet 3 abuts against the lateral sound guiding aperture 4. The first profiled tubular rivet 5 is disposed at the other end of the sound guiding pore D in the lower head body 2 in interference fit. An outside surface 51 of a head portion of the first profiled tubular rivet 5 is matching with the lower sound collecting surface 23 of the lower head body 2. A rod potion of the tubular rivet 5 is closely fitted with the sound guiding pore D. A rod chamber 52 of the first profiled tubular rivet 5 runs through two ends of the first profiled tubular rivet 5 along an axis thereof. An end 53 of the rod portion of the first profiled tubular rivet 5 abuts against the lateral sound guiding aperture 4.

Figure 8:
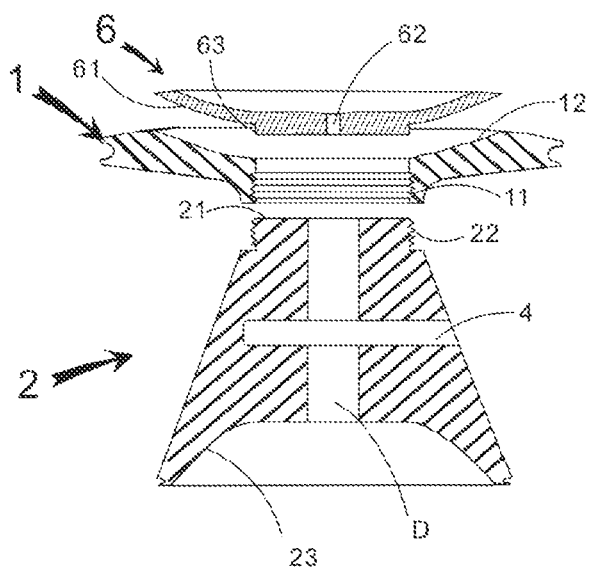
FIG. 8 is a schematic diagram showing an assembly of the present disclosure (where only an upper head body is made of a low-density material)
Figure 9:
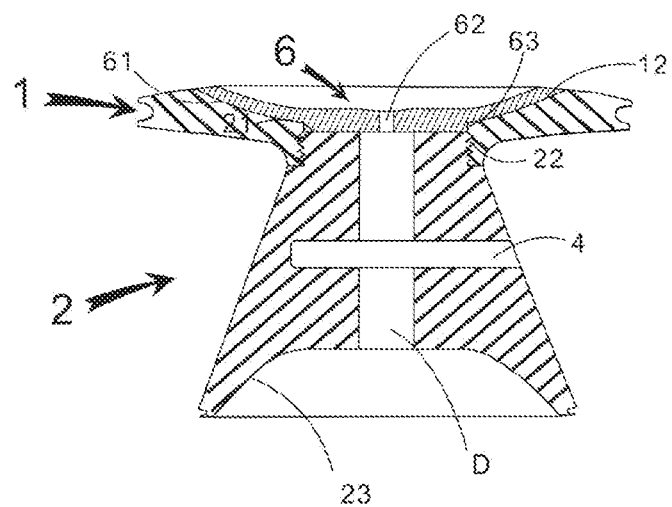
FIG. 9 is a schematic diagram showing an assembly of the present disclosure (where only an upper head body is made of a low-density material)
Figure 10:
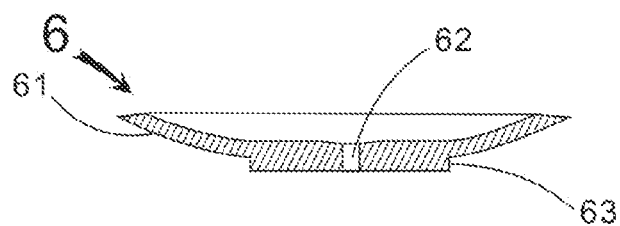
FIG. 10 is a schematic diagram showing a profiled tubular rivet of the present disclosure.
Figure 11:
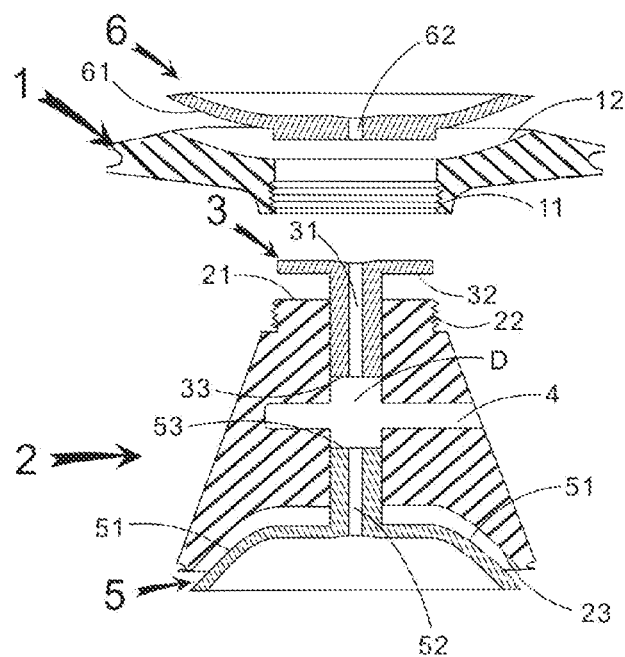
FIG. 11 is a schematic diagram showing an assembly of the present disclosure (where both of an upper head body and a lower head are made of low-density material)
Figure 12:
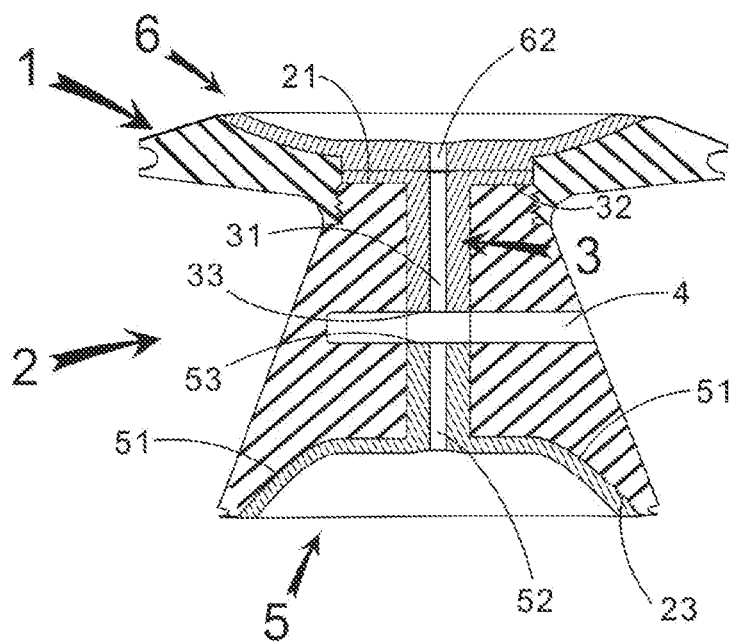
FIG. 12 is a schematic diagram of the present disclosure (where both of an upper head body and a lower head are made of low-density material)

In a fourth embodiment, the present disclosure is further illustrated with reference to FIG. 8, FIG. 9 and FIG. 10.

A stethoscope head consists of an upper head body 1, a lower head body 2, an upper sound collecting surface 12 which is curved and located on the upper head body 1, a lower sound collecting surface 23 which is located on the lower head body 2 and is opposite to the upper sound collecting surface 12, a lateral sound guiding aperture 4 disposed in the lower head body 2 and a second profiled tubular rivet 6.

The upper head body 1 is provided with an internal thread 11, and the lower head body 2 is provided with an external thread 22, so that the upper head body 1 and the lower head body 2 are fixed together through the cooperation between the internal thread 11 and the external thread 22.

A sound guiding pore D runs through the upper head body 1 and the lower head body 2, so that the upper sound collecting surface 12 is communicated with the lower sound collecting surface 23 through the sound guiding pore D. The sound guiding pore D is communicated with and intersects with the lateral sound guiding aperture 4.

The upper head body 1 is made of engineering rubber, and the lower head body 2 is made of zinc alloy material.

A second profiled tubular rivet 6 is disposed at one end of the sound guiding pore D in the upper head body 1 by an interference fit. An outside surface 61 of a head portion of the second profiled tubular rivet 6 is shape-matching with the upper sound collecting surface 12 of the upper head body 1. A chamber 62 in a rod portion 63 of the second profiled tubular rivet 6 runs through both ends of the second profiled tubular rivet 6. The rod portion 63 is disposed in the sound guiding pore D, where an outside surface of the rod portion 63 is closely fitted with an inner wall of the sound guiding pore D. Another end of the sound guiding pore D in the upper head body 1 is provided with the internal thread 11 which is fitted with the lower head body 2.

In a fifth embodiment, the present disclosure is further illustrated with reference to FIG. 4, FIG. 5, FIG. 6, FIG. 7, FIG. 10, FIG. 11 and FIG. 12.

A stethoscope head consists of an upper head body 1, a lower head body 2, an upper sound collecting surface 12 which located on the upper head body 1, a lower sound collecting surface 23 which is located on the lower head body 2 and is opposite to the upper sound collecting surface 12, a lateral sound guiding aperture 4 and a sound guiding pore D which are disposed in the lower head body 2, a tubular rivet 3 and a first profiled tubular rivet 5.

The upper head body 1 is provided with an internal thread 11, and the lower head body 2 is provided with an external thread 22, so that the upper head body 1 and the lower head body 2 are fixed together through the cooperation between the internal thread 11 and the external thread 22.

The sound guiding pore D runs through the upper head body 1 and the lower head body 2, so that the upper sound collecting surface 12 is communicated with the lower sound collecting surface 23 through the sound guiding pore D. The sound guiding pore D is communicated with and intersects with the lateral sound guiding aperture 4.

In the case that both of the upper head body 1 and the lower head body 2 are made of engineering plastics or engineering rubber, the tubular rivet 3 and the first profiled tubular rivet 5 may be made of material such as copper (with a density of 8.9 g/cm$^3$), titanium alloy (with a density of 7.82 g/cm$^3$), stainless steel, steel (with a density of 7.8 g/cm$^3$), zinc alloy (with a density of 6.58 g/cm$^3$) or aluminium alloy (with a density of 2.7 g/cm$^3$), which has a density larger than that of engineering plastics or engineering rubber.

In the case that both of the upper head body 1 and the lower head body 2 are made of the aluminium alloy, the tubular rivet 3 and the first profiled tubular rivet 5 may be made of material such as copper (with a density of 8.9 g/cm$^3$), titanium alloy (with a density of 7.82 g/cm$^3$), steel (with a density of 7.8 g/cm$^3$), and zinc alloy (with a density of 6.58 g/cm$^3$), which has a density larger than that of the aluminium alloy.

The second profiled tubular rivet 6 is disposed at one end of the sound guiding pore D in the upper head body 1 by an interference fit. An outside surface 61 of a head portion of the second profiled tubular rivet 6 is matching with the upper sound collecting surface 12 on the upper head body 1. A chamber 62 in the rod portion of the second profiled tubular rivet 6 runs through both ends of the second profiled tubular rivet 6. The other end of the sound guiding pore D in the upper head body 1 is provided with the internal thread 11 which matches with the lower head body 2.

The tubular rivet 3 is disposed at one end of the sound guiding pore D in the lower head body 2 by an interference fit. A rod chamber 31 of the tubular rivet 3 runs through two ends of the tubular rivet 3 along an axis of the tubular rivet 3. A cap portion 32 of the tubular rivet 3 is closely fitted with an end surface 21 of the lower head body 2 and is shape-matching with the end surface 21 of the lower head body 2. A rod portion 33 of the tubular rivet abuts against the lateral sound guiding aperture 4. The first profiled tubular rivet 5 is disposed at the other end of the sound guiding pore D in the lower head body 2 by an interference fit. An outside surface 51 of a head portion of the first profiled tubular rivet 5 is shape-matching with the lower sound collecting surface 23 of the lower head body 2, and a rod chamber 52 of the first profiled tubular rivet 5 runs through two ends of the first profiled tubular rivet 5 along an axis thereof. An end 53 of the rod portion of the first profiled tubular rivet 5 abuts against the lateral sound guiding aperture 4.

In a sixth embodiment, the present disclosure is further illustrated with reference to FIG. 13, FIG. 14, FIG. 15 and FIG. 16.

A stethoscope head includes a head body 8 and a sound guiding conduit formed in the head body. The sound guiding conduit includes a sound collecting surface, a sound guiding pore D and a lateral sound guiding aperture 4. The sound collecting surface includes an upper sound collecting surface 12 and a lower sound collecting surface 23.

The head body 8 is integral and made of engineering rubber.

A sound guiding layer on the upper sound collecting surface 12 is composed of a first profiled tubular rivet 5 made of copper. A sound guiding layer on the lower sound collecting surface 23 is composed of a third profiled tubular rivet 7 made of titanium alloy.

Further, an outside surface 51 of a head portion of the first profiled tubular rivet 5 is shape-matching with and closely fitted with the upper sound collecting surface 12 of the head body 8. An outside surface of a rod portion of the first profiled tubular rivet 5 is closely fitted with the sound guiding pore D. An outside surface 71 of a head portion of the third profiled tubular rivet 7 is shape-matching with and closely fitted with the lower sound collecting surface 23 of the head body 8. An outside surface of a rod portion 73 of the third profiled tubular rivet 7 is closely fitted with the sound guiding pore D.

Further, a rod chamber 52 of the first profiled tubular rivet 5 runs through two ends of the first profiled tubular rivet 5 and is communicated with the lateral sound guiding aperture 4. A rod chamber 72 of the third profiled tubular rivet 7 runs through two ends of the third profiled tubular rivet 7 and is communicated with the lateral sound guiding aperture 4.

Figure 13:
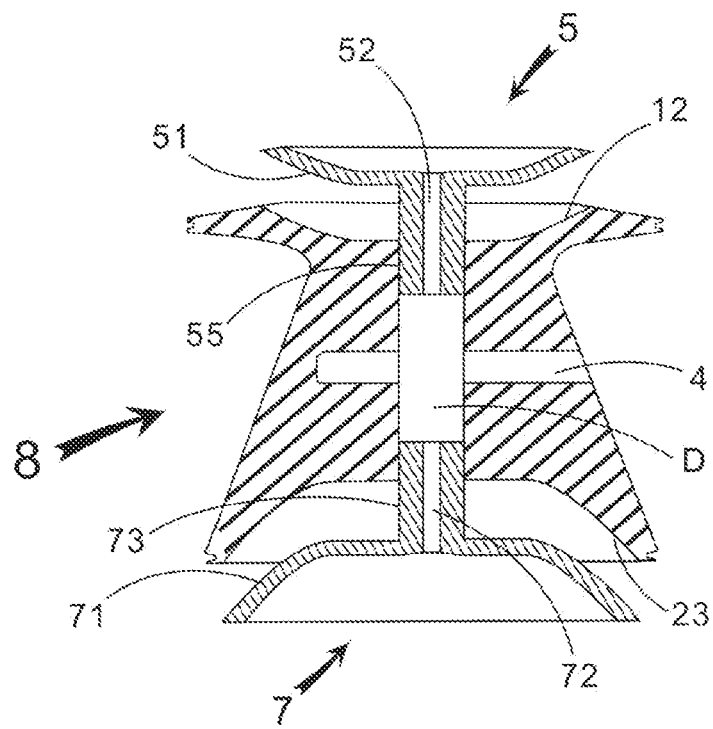
FIG. 13 is a schematic diagram of the present disclosure (where a head body is integrated).
Figure 14:
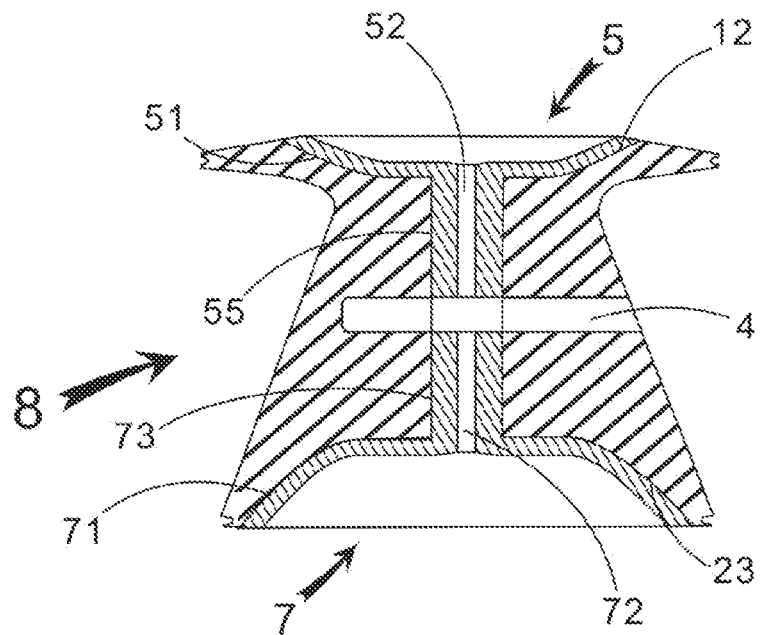
FIG. 14 is a schematic diagram of the present disclosure (where a head body is integrated).

Referring to FIG. 13 and FIG. 14, an end of the rod portion of the first profiled tubular rivet 5 abuts against and is communicated with the lateral sound guiding aperture 4. An end of the rod portion of the third profiled tubular rivet 7 abuts against and is communicated with the lateral sound guiding aperture 4.

Figure 15:
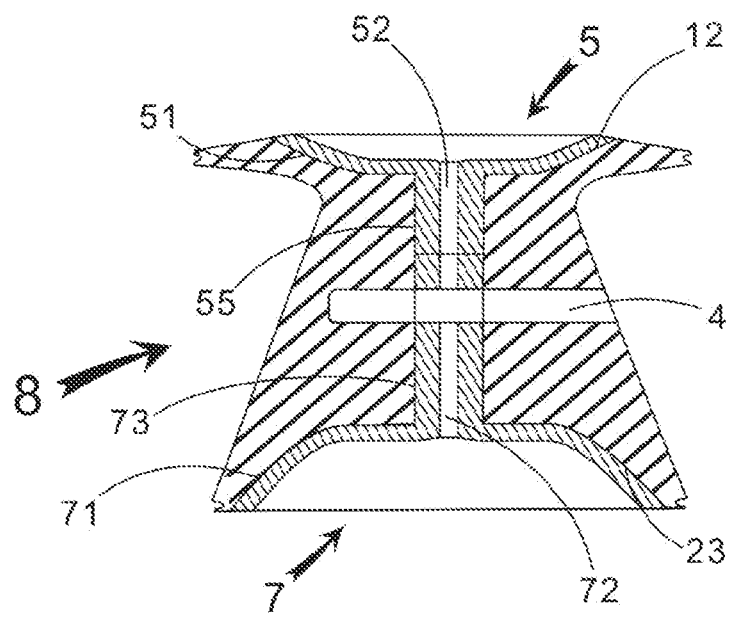
FIG. 15 is a schematic diagram of the present disclosure (where a head body is integrated).

Further referring to FIG. 15, a through hole, which is coaxial with the lateral sound guiding aperture 4 and has a bore diameter same as that of the lateral sound guiding aperture 4, is formed in the rod portion 73 of the third profiled tubular rivet 7 and opens on the wall of the rod portion 73, and is communicated with the rod chamber. An end of the rod portion of the first profiled tubular rivet 5 abuts against that of the third profiled tubular rivet 7.

Figure 16:
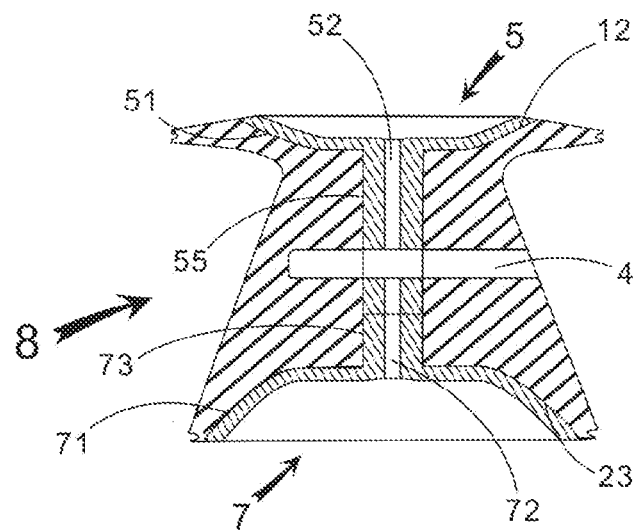
FIG. 16 is a schematic diagram of the present disclosure (where a head body is integrated).

Alternatively, referring to FIG. 16, a through hole, which is coaxial with the lateral sound guiding aperture 4 and has a bore diameter same as that of the lateral sound guiding aperture 4, is formed in the rod portion 55 of the first profiled tubular rivet 5 and opens on the wall of the rod portion 55, and is communicated with the rod chamber 52. An end of the rod portion of the third profiled tubular rivet 7 abuts against that of the first profiled tubular rivet 5.

In a seventh embodiment, the present disclosure is further illustrated with reference to FIG. 13, FIG. 14, FIG. 15 and FIG. 16.

The present embodiment of the present invention provides a method for manufacturing a stethoscope head with a reduced weight, and the stethoscope head includes a head body 8 and a sound guiding conduit formed in the head body. The sound guiding conduit includes an upper sound collecting surface 12, a lower sound collecting surface 23, a sound guiding pore D and a lateral sound guiding aperture 4.

A first profiled tubular rivet 5 and a third profiled tubular rivet 7 are made of stainless steel.

The head body 8, which may be assembled or integral, may be made of engineering plastics.

An outside surface 51 of a head portion of the first profiled tubular rivet 5 is shape-matching with and closely fitted with the upper sound collecting surface 12 of the head body 8. An outside surface of a rod portion 55 of the first profiled tubular rivet 5 is closely fitted with the sound guiding pore D.

An outer surface 71 of a head portion of the third profiled tubular rivet 7 is shape-matching with and closely fitted with the lower sound collecting surface 23 of the head body 8. An outside surface of a rod portion of the third profiled tubular rivet 7 is closely fitted with the sound guiding pore D.

In an eighth embodiment, the present disclosure is further illustrated with reference to FIG. 9.

The present embodiment of the present invention provides a method for manufacturing a stethoscope head with a reduced weight, and the stethoscope head includes an upper head body 1, a lower head body 2 and a second profiled tubular rivet 6.

The upper head body 1 is provided with a curved upper sound collecting surface 12, and the lower head body 2 is provided with a lower sound collecting surface 23 and a lateral sound guiding aperture 4, where the upper head body 1 is provided with an internal thread 11, and the lower head body 2 is provided with an external thread 22, so that the upper head body 1 and the lower head body 2 are fixed together through a fit of the internal thread 11 and the external thread 22.

A sound guiding pore D runs through the upper head body 1 and the lower head body 2, so that the upper sound collecting surface 12 is communicated with the lower sound collecting surface 23 through the sound guiding pore D. The sound guiding pore D is communicated with and intersects the lateral sound guiding aperture 4.

The upper head body 1 is made of engineering rubber.
The lower head body 2 is made of stainless steel.
The second profiled tubular rivet 6 is made of aluminium alloy.

A second profiled tubular rivet 6 is disposed at one end of the sound guiding pore D in the upper head body 1 by an interference fit. An outside surface 61 of a head portion of the second profiled tubular rivet 6 is shape-matching with the upper sound collecting surface 12, a chamber 62 in the rod portion of the second profiled tubular rivet 6 runs through both ends of the second profiled tubular rivet 6, and the other end of the sound guiding pore D in the upper head body 1 is provided with the internal thread 11 fitted with the lower head body 2.

Compared with the prior art, the present disclosure has benefits further illustrated below.

For example, an exemplary stethoscope in the prior art is manufactured by Wuxi Kaishun Medical Device Manufacturing CO., Ltd.

In the detection below, a sound collecting chamber refers to a chamber formed by fixing a diaphragm over the sound collecting surface of the head body.

A method for testing a sound conducting performance of the stethoscope includes steps as below.

First, the sound collecting chamber of the stethoscope head is placed on a sealing connector of a sound generator such that the sound collecting surface (i.e. the diaphragm) of the stethoscope head rightly faces a sound output port of the sound generator, and a joint between an outward face of the sound collecting surface and an inward face of the sound output port of the sound generator is in sealed status. A distance between the sound output port of the sound generator and the sound collecting surface of the stethoscope head is in a range from 8 mm to 10 mm.

Secondly, one end of a sound conducting tube with a diameter of 10 mm, a bore diameter of 4 mm and a length of 40 cm is connected to a sound conducting connector of the stethoscope head, and the other end of the sound conducting tube is connected to an audio receiver.

Thirdly, the sound generator and the audio receiver are turned on, a numerical value detected by the audio receiver is recorded and is divided by a standard numerical value of the sound generator to obtain a quotient, which is used for obtaining the sound conducting performance of the stethoscope.

A method for testing external noise resistance of the stethoscope includes steps as below.

First, a back surface of the sound collecting chamber of the stethoscope head is placed on the sealing connector of the sound generator such that the back surface of the sound collecting surface of the stethoscope head rightly faces the sound output port of the sound generator, and a joint between an outward face of the sound collecting surface and an inward face of the sound output port of the sound generator is in sealed status. The distance between the sound output port of the sound generator and the sound collecting surface of the stethoscope head is in a range from 4 mm to 6 mm.

Secondly, one end of the sound conducting tube with a diameter of 10 mm, an aperture of 4 mm and a length of 40 cm is connected to a sound conducting connector of the stethoscope head, and the other end of the sound conducting tube is connected to an audio receiver.

Thirdly, the sound generator and the audio receiver are turned on, a numerical value detected by the audio receiver is recorded and is divided by a standard numerical value of the sound generator to obtain a quotient, which is used for obtaining the external noise resistance of the stethoscope.

Comparing Example 1 from comparison of the stethoscope of the first embodiment of the present invention with stethoscopes of KS-410A, KS-410B and KS-410C types manufactured by Wuxi Kaishun Medical Device Manufacturing CO., Ltd, it can be known that time for manufacturing the inventive stethoscope is saved by about a quarter, a cost for manufacturing the inventive stethoscope is saved by more than one third, the external noise resistance of the inventive stethoscope is improved by about one fifth, and a weight of the inventive stethoscope is reduced by about one third, without significant change to the sound conducting performance, further, the inventive stethoscope is easy to carry and has a good appearance.

Comparative data of a stethoscope of the first embodiment of the present disclosure with the KS-410A type of stethoscope are shown below.

| Type of stethoscope with single sound collecting surface | The inventive stethoscope | KS-410A | Data comparison result |
|---|---|---|---|
| Structure | Individually made of a combination of high density material and low density material | Made of only high density material | |
| Name of high density material | Stainless steel (type 304) | Stainless steel (type 304) | |
| Material consumption and cost | 30 grams × CNY 0.035 per gram = CNY 1.05 | 85 grams × CNY 0.035 per gram = CNY 2.97 | |
| Name of low-density material | Polyformaldehyde (POM) | | |
| Material consumption and cost | 14 grams × CNY 0.025 per gram = CNY 0.35 | | |
| Cutting tool consumption | CNY 1.85 | CNY 2.23 | |
| Machining time and cost | 258 sec × CNY 0.011 per second = CNY 2.86 | 341 sec × CNY 0.011 per second = CNY 3.75 | Machining time is saved by 24% |
| Total cost | CNY 6.11 | CNY 8.95 | Total cost is save by 32% |
| Sound conducting performance test (where a sound is collected by a sound collecting chamber of the stethoscope) | Sound source: 114 dB 1000 HZ Measured value: 109 dB Sound source: 114 dB 500 HZ Measured value: 102 dB | Sound source: 114 dB 1000 HZ Measured value: 109.6 dB Sound source: 114 dB 500 HZ Measured value: 101 dB | Sound conducting performance has no significant change |
| External noise resistance | Sound source: 114 dB 1000 HZ | Sound source: 114 dB 1000 HZ | External noise |

-continued

| Type of stethoscope with single sound collecting surface | The inventive stethoscope | KS-410A | Data comparison result |
|---|---|---|---|
| performance test (where a sound is collected by a back of the stethoscope) | Measured value: 35 dB Sound source: 114 dB 500 HZ Measured value: 28 dB | Measured value: 42.6 dB Sound source: 114 dB 500 HZ Measured value: 35.3 dB | resistance is improved by 18% to 21% |
| Aesthetics (two colors mixed) | With two colors mixed | Monochrome | Visual effect is improved |
| Portability (in weight) | 44 grams | 85 grams | Easy to carry |

Comparative data of a stethoscope of the first embodiment of the present disclosure with the KS-410B type of stethoscope are shown below.

| Type of stethoscope with single sound collecting surface | The inventive stethoscope | KS-410B | Data comparison result |
|---|---|---|---|
| Structure | Individually made of a combination of high density material and low density material | Made of only high density material | |
| Name of high density material | Stainless steel (type 304) | Stainless steel (type 304) | |
| Material consumption and cost | 35 grams × CNY 0.035 per gram = CNY 1.22 | 95 grams × CNY 0.035 per gram = CNY 3.32 | |
| Name of low-density material | Polyformaldehyde (POM) | | |
| Material consumption and cost | 17 grams × CNY 0.025 per gram = CNY 0.42 | | |
| Cutting tool consumption | CNY 1.65 | CNY 2.11 | |
| Machining time and cost | 276 second × CNY 0.011 per second = CNY 3.03 | 375 second × CNY 0.011 per second = CNY 4.12 | Machining time is saved by 26% |
| Total cost | CNY 6.32 | CNY 9.55 | Total cost is save by 34% |
| Sound conducting performance test (where a sound is collected by a sound collecting chamber of the stethoscope) | Sound source: 114 dB 1000 HZ Measured value: 110 dB Sound source: 114 dB 500 HZ Measured value: 101 dB | Sound source: 114 dB 1000 HZ Measured value: 109.5 dB Sound source: 114 dB 500 HZ Measured value: 102.3 dB | Sound conducting performance has no significant change |
| External noise resistance performance test (where a sound is collected by a back of the stethoscope) | Sound source: 114 dB 1000 HZ Measured value: 34 dB Sound source 114 dB 500 HZ Measured value: 26.4 dB | Sound source: 114 dB 1000 HZ Measured value: 43 dB Sound source 114 dB 500 HZ Measured value: 36.1 dB | External noise resistance is improved by 21% to 27% |
| Aesthetics (two colors mixed) | With two colors mixed | Monochrome | Visual effect is improved |
| Portability (in weight) | 52 grams | 95 grams | Easy to carry |

Comparative data of a stethoscope of the first embodiment of the present disclosure with the KS-410C type of stethoscope are shown below.

| Type of stethoscope with single sound collecting surface | The inventive stethoscope | KS-410C | Data comparison result |
|---|---|---|---|
| Structure | Individually made of a combination of high density material and low density material | Made of only high density material | |

-continued

| Type of stethoscope with single sound collecting surface | The inventive stethoscope | KS-410C | Data comparison result |
|---|---|---|---|
| Name of high density material | Stainless steel (type 304) | Stainless steel(type 304) | |
| Material consumption and cost | 33 grams × CNY 0.035 per gram = CNY 1.155 | 87 grams × CNY 0.035 per gram = CNY 3.045 | |
| Name of low-density material | Polyformaldehyde (POM) | | |
| Material consumption and cost | 18 grams × CNY 0.025 per gram = CNY 0.45 | | |
| Cutting tool consumption | CNY 1.75 | CNY 2.08 | |
| Machining time and cost | 278 second × CNY 0.011 second = CNY 3.05 | 374 second × CNY 0.011 per second = CNY 4.11 | Machining time is saved by 26% |
| Total cost | CNY 6.41 | CNY 9.23 | Total cost is save by 31% |
| Sound conducting performance test (where a sound is collected by a sound collecting chamber of the stethoscope) | Sound source: 114 dB 1000 HZ Measured value: 107 dB Sound source: 114 dB 500 HZ Measured value: 101.2 dB | Sound source: 114 dB 1000 HZ Measured value: 108 dB Sound source: 114 dB 500 HZ Measured value: 102 dB | Sound conducting performance has no significant change |
| External noise resistance performance test (where a sound is collected by a back of the stethoscope) | Sound source: 114 dB 1000 HZ Measured value: 38 dB Sound source: 114 dB 500 HZ Measured value: 27.3 dB | Sound source: 114 dB 1000 HZ Measured value: 43.5 dB Sound source: 114 dB 500 HZ Measured value: 36.1 dB | External noise resistance is improved by 13% to 25% |
| Aesthetics (two colors mixed) | With two colors mixed | Monochrome | Visual effect is improved |
| Portability (in weight) | 50 grams | 90 grams | Easy to carry |

Comparing Example 2 from comparison of the stethoscope of the second embodiment of the present invention with stethoscopes of KS-450A, KS-450B and KS-450C types manufactured by Wuxi Kaishun Medical Device Manufacturing CO., Ltd, it can be known that time for manufacturing the inventive stethoscope is saved by about a quarter, a cost for manufacturing the inventive stethoscope is reduced by about one third, the external noise resistance of the inventive stethoscope is improved by about one fifth, a weight of the inventive stethoscope is reduced by about one third, without significant change to the sound conducting performance, further the inventive stethoscope is easy to carry and has a good appearance.

Comparative data of a stethoscope of the second embodiment of the present disclosure with the KS-450A type of stethoscope are shown below.

| Type of stethoscope with single sound collecting surface | The inventive stethoscope | KS-450A | Data comparison result |
|---|---|---|---|
| Structure | Integrated combination of high density material and low density material formed by injection molding | Made of only high density material | |
| Name of high density material | Stainless steel (type 304) | Stainless steel(type 304) | |
| Material consumption and cost | 32 grams × CNY 0.035 per gram = CNY 1.12 | 87 grams × CNY 0.035 per gram = CNY 3.04 | |
| Name of low-density material | Polyformaldehyde (POM) | | |
| Material consumption and cost | 19 grams × CNY 0.025 per gram = CNY 0.48 | | |
| Cutting tool consumption | CNY 1.13 | CNY 2.24 | |
| Machining time and cost | 212 second × CNY 0.011 per second = CNY 2.33 | 381 second × CNY 0.011 per second = CNY 4.19 | Machining time is saved by 26% |

-continued

| Type of stethoscope with single sound collecting surface | The inventive stethoscope | KS-450A | Data comparison result |
|---|---|---|---|
| Total cost | CNY 5.6 | CNY 9.4 | Total cost is save by 39% |
| Sound conducting performance test (where a sound is collected by a sound collecting chamber of the stethoscope) | Sound source: 114 dB 1000 HZ Measured value: 110 dB Sound source: 114 dB 500 HZ Measured value: 101 dB | Sound source: 114 dB 1000 HZ Measured value: 109.5 dB Sound source: 114 dB 500 HZ Measured value: 102.3 dB | Sound conducting performance has no significant change |
| External noise resistance performance test (where a sound is collected by a back of the stethoscope) | Sound source: 114 dB 1000 HZ Measured value: 31.3 dB Sound source: 114 dB 500 HZ Measured value: 26.7 dB | Sound source: 114 dB 1000 HZ Measured value: 39.8 dB Sound source: 114 dB 500 HZ Measured value: 36.9 dB | External noise resistance is improved by 21% to 28% |
| Aesthetics (two colors mixed) | With two colors mixed | Monochrome | Visual effect is improved |
| Portability (in weight) | 51 grams | 87 grams | Easy to carry |

Comparative data of a stethoscope of the second embodiment of the present disclosure with the KS-450B type of stethoscope are shown below.

| Type of stethoscope with single sound collecting surface | The inventive stethoscope | KS-450B | Data comparison result |
|---|---|---|---|
| Structure | Integrated combination of high density material and low density material formed by injection molding | Made of only high density material | |
| Name of high density material | Stainless steel (type 304) | Stainless steel (type 304) | |
| Material consumption and cost | 37 grams × CNY 0.035 per gram = CNY 1.29 | 90 grams × CNY 0.035 per gram = CNY 3.15 | |
| Name of low-density material | Polyformaldehyde (POM) | | |
| Material consumption and cost | 17 grams × CNY 0.025 per gram = CNY 0.42 | | |
| Cutting tool consumption | CNY 1.23 | CNY 2.30 | |
| Machining time and cost | 225 sec × CNY 0.011 per sec = CNY 2.47 | 390 sec × CNY 0.011 per sec = CNY 4.29 | Machining time is saved by 43 |
| Total cost | CNY 5.41 | CNY 9.74 | Total cost is save by 45 |
| Sound conducting performance test (where a sound is collected by a sound collecting chamber of the stethoscope) | Sound source: 114 dB 1000 HZ Measured value: 111 dB Sound source: 114 dB 500 HZ Measured value: 103 dB | Sound source: 114 dB 1000 HZ Measured value: 108.5 dB Sound source: 114 dB 500 HZ Measured value: 101.6 dB | Sound conducting performance has no significant change |
| External noise resistance performance test (where a sound is collected by a back of the stethoscope) | Sound source: 114 dB 1000 HZ Measured value: 32.2 dB Sound source: 114 dB 500 HZ Measured value: 29 dB | Sound source: 114 dB 1000 HZ Measured value: 38.1 dB Sound source: 114 dB 500 HZ Measured value: 37 dB | External noise resistance is improved by 16% to 22% |
| Aesthetics (two colors mixed) | With two colors mixed | Monochrome | Visual effect is improved |
| Portability (in weight) | 53 grams | 88 grams | Easy to carry |

Comparative data of a stethoscope of the second embodiment of the present disclosure with the KS-450C type of stethoscope are shown below.

| Type of stethoscope with single sound collecting surface | The inventive stethoscope | KS-450C | Data comparison result |
|---|---|---|---|
| Structure | Integrated combination of high density material and low density material formed by injection molding | Made of only high density material | |
| Name of high density material | Stainless steel (type 304) | Stainless steel(type 304) | |
| Material consumption and cost | 33 grams × CNY 0.035 per gram = CNY 1.15 | 85 grams × CNY 0.035 per gram = CNY 2.97 | |
| Name of low-density material | Polyformaldehyde (POM) | | |
| Material consumption and cost | 21 grams × CNY 0.025 per gram = CNY 0.52 | | |
| Cutting tool consumption | CNY 1.07 | CNY 2.5 | |
| Machining time and cost | 234 sec × CNY 0.011 per second = CNY 2.57 | 395 sec × CNY 0.011 per second = CNY 4.34 | Machining time is saved by 41 |
| Total cost | CNY 5.31 | CNY 9.81 | Total cost is save by 46 |
| Sound conducting performance test (where a sound is collected by a sound collecting chamber of the stethoscope) | Sound source: 114 dB 1000 HZ Measured value: 108.2 dB Sound source: 114 dB 500 HZ Measured value: 109.1 dB | Sound source: 114 dB 1000 HZ Measured value: 106 dB Sound source: 114 dB 500 HZ Measured value: 105.2 dB | Sound conducting performance has no significant change |
| External noise resistance performance test (where a sound is collected by a back of the stethoscope) | Sound source: 114 dB 1000 HZ Measured value: 33.6 dB Sound source: 114 dB 500 HZ Measured value: 28.2 dB | Sound source: 114 dB 1000 HZ Measured value: 41.1 dB Sound source: 114 dB 500 HZ Measured value: 38.4 dB | External noise resistance is improved by 19% to 27% |
| Aesthetics (two colors mixed) | With two colors mixed | Monochrome | Visual effect is improved |
| Portability (in weight) | 55 grams | 84 grams | Easy to carry |

Comparing Example 3 a stethoscope of the third embodiment of the present invention (where an upper head body is made of a high density material, a lower head body is made of a combination of a high density material and a low density material) is compared with stethoscopes of KS-500A, KS-500B and KS-500C types manufactured by Wuxi Kaishun Medical Device Manufacturing CO., Ltd.

Comparative data of a stethoscope of the third embodiment of the present disclosure with the KS-500A type of stethoscope are shown below.

| Type of stethoscope with two sound collecting surfaces | The inventive stethoscope | KS-500A | Data comparison result |
|---|---|---|---|
| Structure | Upper head body is made of only high density material, a lower head body is made of combination of high density material and low density material | Made of only high density material | |
| Name of high density material | Stainless steel (type 304) | Stainless steel(type 304) | |
| Material consumption and cost | 55 grams × CNY 0.035 per gram = CNY 1.93 | 98 grams × CNY 0.035 per gram = CNY 3.43 | |
| Name of low-density material | Polyformaldehyde (POM) | | |
| Material consumption and cost | 12 grams × CNY 0.025 per gram = 0.3 | | |

-continued

| Type of stethoscope with two sound collecting surfaces | The inventive stethoscope | KS-500A | Data comparison result |
|---|---|---|---|
| Cutting tool consumption | 2.32 | 2.74 | |
| Machining time and cost | 315 second × CNY 0.011 per second = CNY 3.47 | 453 second × CNY 0.011 per second = CNY 4.98 | Machining time is saved by 31% |
| Total cost | CNY 8.02 | CNY 11.15 | Total cost is save by 28% |
| Sound conducting performance test (where a sound is collected by a sound collecting chamber of the stethoscope) | Sound source: 114 dB 1000 HZ Measured value: 113 dB Sound source: 113 dB 500 HZ Measured value: 103 dB | Sound source: 114 dB 1000 HZ Measured value: 112.7 dB Sound source: 114 dB 500 HZ Measured value: 102.5 dB | Sound conducting performance has no significant change |
| External noise resistance performance test (where a sound is collected by a back of the stethoscope) | Sound source: 114 dB 1000 HZ Measured value: 32.5 dB Sound source: 114 dB 500 HZ Measured value: 25.1 dB | Sound source: 114 dB 1000 HZ Measured value: 41.4 dB Sound source: 114 dB 500 HZ Measured value: 34.8 dB | External noise resistance is improved by 20% |
| Aesthetics (two colors mixed) | With two colors mixed | Monochrome | Visual effect is improved |
| Portability (in weight) | 67 grams | 98 grams | Easy to carry |

Comparative data of a stethoscope of the third embodiment of the present disclosure with the KS-500B type of stethoscope are shown below.

| Type of stethoscope with two sound collecting surfaces | The inventive stethoscope | KS-500B | Data comparison result |
|---|---|---|---|
| Structure | Upper head body is made of only high density material, lower head body is made of combination of high density material and low density material | Made of only high density material | |
| Name of high density material | Stainless steel (type 304) | Stainless steel (type 304) | |
| Material consumption and cost | 53 grams × CNY 0.035 per gram = CNY 1.85 | 96 grams × CNY 0.035 per gram = CNY 3.36 | |
| Name of low-density material | Polyformaldehyde (POM) | | |
| Material consumption and cost | 11 grams × CNY 0.025 per gram = CNY 0.27 | | |
| Cutting tool consumption | 2.22 | 2.61 | |
| Machining time and cost | 327 second × CNY 0.011 per second = CNY 3.59 | 466 second × CNY 0.011 per second = CNY 5.12 | Machining time is saved by 30% |
| Total cost | CNY 7.93 | CNY 11.09 | Total cost is save by 29% |
| Sound conducting performance test (where a sound is collected by a sound collecting chamber of the stethoscope) | Sound source: 114 dB 1000 HZ Measured value: 122.3 dB Sound source: 113 dB 500 HZ Measured value: 110.2 dB | Sound source: 114 dB 1000 HZ Measured value: 113.4 dB Sound source: 114 dB 500 HZ Measured value: 106.6 dB | Sound conducting performance has no significant change |
| External noise resistance performance test (where a sound is collected by a back of the stethoscope) | Sound source: 114 dB 1000 HZ Measured value: 35.1 dB Sound source: 114 dB 500 HZ Measured value: 27.5 dB | Sound source: 114 dB 1000 HZ Measured value: 43.2 dB Sound source: 114 dB 500 HZ Measured value: 37.4 dB | External noise resistance is improved by 19% to 27% |

-continued

| Type of stethoscope with two sound collecting surfaces | The inventive stethoscope | KS-500B | Data comparison result |
|---|---|---|---|
| Aesthetics (two colors mixed) | With two colors mixed | Monochrome | Visual effect is improved |
| Portability (in weight) | 69 grams | 100 grams | Easy to carry |

Comparative data of a stethoscope of the third embodiment of the present disclosure with the KS-500C type of stethoscope are shown below.

| Type of stethoscope with two sound collecting surfaces | The inventive stethoscope | KS-500C | Data comparison result |
|---|---|---|---|
| Structure | Upper head body is made of only high density material, lower head body is made of combination of high density material and low density material | Made of only high density material | |
| Name of high density material | Stainless steel (type 304) | Stainless steel(type 304) | |
| Material consumption and cost | 57 grams × CNY 0.035 per gram = CNY 1.99 | 100 grams × CNY 0.035 per gram = CNY 3.5 | |
| Name of low-density material | Polyformaldehyde (POM) | | |
| Material consumption and cost | 15 grams × CNY 0.025 per gram = CNY 0.37 | | |
| Cutting tool consumption | CNY 2.5 | CNY 2.88 | |
| Machining time and cost | 332 second × CNY 0.011 per second = CNY 3.65 | 477 second × CNY 0.011 per second = CNY 5.24 | Machining time is saved by 31% |
| Total cost | CNY 8.51 | CNY 11.62 | Total cost is save by 27% |
| Sound conducting performance test (where a sound is collected by a sound collecting chamber of the stethoscope) | Sound source: 114 dB 1000 HZ Measured value: 131.2 dB Sound source: 114 dB 500 HZ Measured value: 105.5 dB | Sound source: 114 dB 1000 HZ Measured value: 120.4 dB Sound source: 114 dB 500 HZ Measured value: 108.8 dB | Sound conducting performance has no significant change |
| External noise resistance performance test (where a sound is collected by a back of the stethoscope) | Sound source: 114 dB 1000 HZ Measured value: 34.5 dB Sound source: 114 dB 500 HZ Measured value: 25.1 dB | Sound source: 114 dB 1000 HZ Measured value:41.4 dB Sound source: 114 dB 500 HZ Measured value: 34.8 dB | External noise resistance is improved by 17% to 28% |
| Aesthetics (two colors mixed) | With two colors mixed | Monochrome | Visual effect is improved |
| Portability (in weight) | 75 grams | 102 grams | Easy to carry | it can be known from the above comparative data that in the present disclosure, a time for manufacturing the inventive stethoscope is saved by about 30%, a cost for manufacturing the inventive stethoscope is reduced by about 30%, the external noise resistance of the inventive stethoscope is improved by about 20%, a weight of the inventive stethoscope is reduced by about 30%, without significant change to the sound conducting performance, and the stethoscope is easy to carry and has a good appearance.

Comparing Example 4 a stethoscope of the forth embodiment of the present invention (where an upper head body is made of a combination of a high density material and a low density material, a lower head body is made of only a high density material) is compared with stethoscopes of KS-510A, KS-510B and KS-510C types manufactured by Wuxi Kaishun Medical Device Manufacturing CO., Ltd.

Comparative data of a stethoscope of the forth embodiment of the present disclosure with the KS-510A type of stethoscope are shown below.

| Type of stethoscope with two sound collecting surfaces | The inventive stethoscope | KS-510A | Data comparison result |
|---|---|---|---|
| Structure | Upper head body is made of a combination of high density material and low density material, lower head body is made of only high density material | Made of only high density material | |
| Name of high density material | Stainless steel (type 304) | Stainless steel(type 304) | |
| Material consumption and cost | 65 grams × CNY 0.035 per gram = CNY 2.27 | 98 grams × CNY 0.035 per gram = CNY 3.43 | |
| Name of low-density material | Polyformaldehyde (POM) | | |
| Material consumption and cost | 9 grams × CNY 0.025 per gram = CNY 0.26 | | |
| Cutting tool consumption | 2.13 | 2.72 | |
| Machining time and cost | 306 second × CNY 0.011 per second = CNY 3.47 | 437 second × CNY 0.011 per second = CNY 4.98 | Machining time is saved by 30% |
| Total cost | CNY 8.13 | CNY 11.15 | Total cost is save by 27% |
| Sound conducting performance test (where a sound is collected by a sound collecting chamber of the stethoscope) | Sound source: 114 dB 1000 HZ Measured value: 113.7 dB Sound source: 114 dB 500 HZ Measured value: 101.9 dB | Sound source: 114 dB 1000 HZ Measured value: 113.1 dB Sound source: 114 dB 500 HZ Measured value: 102.4 dB | Sound conducting performance has no significant change |
| External noise resistance performance test (where a sound is collected by a back of the stethoscope) | Sound source: 114 dB 1000 HZ Measured value: 32.7 dB Sound source: 114 dB 500 HZ Measured value: 25.7 dB | Sound source: 114 dB 1000 HZ Measured value: 41.8 dB Sound source: 114 dB 500 HZ Measured value: 34.5 dB | External noise resistance is improved by 20% |
| Aesthetics (two colors mixed) | With two colors mixed | Monochrome | Visual effect is improved |
| Portability (in weight) | 74 grams | 98 grams | Easy to carry |

Comparative data of a stethoscope of the forth embodiment of the present disclosure with the KS-510B type of stethoscope are shown below.

| Type of stethoscope with two sound collecting surfaces | The inventive stethoscope | KS-510A | Data comparison result |
|---|---|---|---|
| Structure | Upper head body is made of a combination of high density material and low density material, lower head body is made of only high density material | Made of only high density material | |
| Name of high density material | Stainless steel (type 304) | Stainless steel(type 304) | |
| Material consumption and cost | 68 grams × CNY 0.035 per gram = CNY 2.38 | 100 grams × CNY 0.035 per gram = CNY 3.5 | |
| Name of low-density material | Polyformaldehyde (POM) | | |
| Material consumption and cost | 9.8 grams × CNY 0.025 per gram = CNY 0.24 | | |
| Cutting tool consumption | CNY 2.47 | CNY 2.89 | |
| Machining time and cost | 321 second × CNY 0.011 per second = CNY 3.53 | 448 second × CNY 0.011 per second = CNY 4.92 | Machining time is saved by 29% |

| Type of stethoscope with two sound collecting surfaces | The inventive stethoscope | KS-510A | Data comparison result |
|---|---|---|---|
| Total cost | CNY 8.62 | CNY 11.31 | Total cost is save by 24% |
| Sound conducting performance test (where a sound is collected by a sound collecting chamber of the stethoscope) | Sound source: 114 dB 1000 HZ Measured value: 121.4 dB Sound source: 114 dB 500 HZ Measured value: 102.4 dB | Sound source: 114 dB 1000 HZ Measured value: 118.7 dB Sound source: 114 dB 500 HZ Measured value: 110.3 dB | Sound conducting performance has no significant change |
| External noise resistance performance test (where a sound is collected by a back of the stethoscope) | Sound source: 114 dB 1000 HZ Measured value: 33.5 dB Sound source: 114 dB 500 HZ Measured value: 28.1 dB | Sound source: 114 dB 1000 HZ Measured value: 45 dB Sound source: 114 dB 500 HZ Measured value: 37.6 dB | External noise resistance is improved by 26% |
| Aesthetics (two colors mixed) | With two colors mixed | Monochrome | Visual effect is improved |
| Portability (in weight) | 77 grams | 101 grams | Easy to carry |

Comparative data of a stethoscope of the forth embodiment of the present disclosure with the KS-510C type of stethoscope are shown below.

It can be known from the above comparative data that time for manufacturing the inventive stethoscope is saved by 30%, a cost for manufacturing the inventive stethoscope is

| Type of stethoscope with two sound collecting surfaces | The inventive stethoscope | KS-510C | Data comparison result |
|---|---|---|---|
| Structure | Upper head body is made of a combination of high density material and low density material, lower head body is made of only high density material | Made of only high density material | |
| Name of high density material | Stainless steel (type 304) | Stainless steel (type 304) | |
| Material consumption and cost | 66.2 grams × CNY 0.035 per gram = CNY 2.31 | 102.2 grams × CNY 0.035 per gram = CNY 3.57 | |
| Name of low-density material | Polyformaldehyde (POM) | | |
| Material consumption and cost | 8.7 grams × CNY 0.025 per gram = CNY 0.21 | | |
| Cutting tool consumption | CNY 2.04 | CNY 2.67 | |
| Machining time and cost | 324 second × CNY 0.011 per second = CNY 3.56 | 455 second × CNY 0.011 per second = CNY 5 | Machining time is saved by 29% |
| Total cost | CNY 8.12 | CNY 11.24 | Total cost is save by 28% |
| Sound conducting performance test (where a sound is collected by a sound collecting chamber of the stethoscope) | Sound source: 114 dB 1000 HZ Measured value: 125.1 dB Sound source: 114 dB 500 HZ Measured value: 104.2 dB | Sound source: 114 dB 1000 HZ Measured value: 116.4 dB Sound source: 114 dB 500 HZ Measured value: 11.2 dB | Sound conducting performance has no significant change |
| External noise resistance performance test (where a sound is collected by a back of the stethoscope) | Sound source: 114 dB 1000 HZ Measured value: 33.2 dB Sound source: 114 dB 500 HZ Measured value: 27.9 dB | Sound source: 114 dB 1000 HZ Measured value: 45 dB Sound source: 114 dB 500 HZ Measured value: 37.3 dB | External noise resistance is improved by 26% to 27% |
| Aesthetics (two colors mixed) | With two colors mixed | Monochrome | Visual effect is improved |
| Portability (in weight) | 79 grams | 96 grams | Easy to carry | reduced by about 30%, the external noise resistance of the inventive stethoscope is improved by about 20%, a weight of the inventive stethoscope is reduced by about one third, without significant change to the sound conducting performance, and the stethoscope is easy to carry and has a good appearance.

Comparing Example 5 a stethoscope of the fifth embodiment of the present invention (where both of an upper head body and a lower head body are made of a combination of a high density material and a low density material) is compared with stethoscopes of KS-520A, KS-520B and KS-520C types manufactured by Wuxi Kaishun Medical Device Manufacturing CO., Ltd.

Comparative data of a stethoscope of the fifth embodiment of the present disclosure with the KS-520A type of stethoscope are shown below.

| Type of stethoscope with two sound collecting surfaces | The inventive stethoscope | KS-520A | Data comparison result |
|---|---|---|---|
| Structure | Both of an upper head body and a lower head body are made of a combination of high density material and low density material | Made of only high density material | |
| Name of high density material | Stainless steel (type 304) | Stainless steel(type 304) | |
| Material consumption and cost | 32 grams × CNY 0.035 per gram = CNY 1.12 | 101 grams × CNY 0.035 per gram = CNY 3.53 | |
| Name of low-density material | Polyformaldehyde (POM) | | |
| Material consumption and cost | 21 grams × CNY 0.025 per gram = CNY 0.52 | | |
| Cutting tool consumption | CNY 2.27 | CNY 2.85 | |
| Machining time and cost | 287 seondc × CNY 0.011 per second = CNY 3.16 | 396 second × CNY 0.011 per second = CNY 4.36 | Machining time is saved by 28% |
| Total cost | CNY 7.07 | CNY 10.74 | Total cost is save by 33% |
| Sound conducting performance test (where a sound is collected by a sound collecting chamber of the stethoscope) | Sound source: 114 dB 1000 HZ Measured value 113.5 dB Sound source: 114 dB 500 HZ Measured value: 103.3 dB | Sound source: 114 dB 1000 HZ Measured value 112.3 dB Sound source: 114 dB 500 HZ Measured value: 102.1 dB | Sound conducting performance has no significant change |
| External noise resistance performance test (where a sound is collected by a back of the stethoscope) | Sound source: 114 dB 1000 HZ Measured value 32.7 dB Sound source: 114 dB 500HZ Measured value: 25.7 dB | Sound source: 114 dB 1000 HZ Measured value 41.9 dB Sound source: 114 dB 500 HZ Measured value: 34.1 dB | External noise resistance is improved by 20% |
| Aesthetics (two colors mixed) | With two colors mixed | Monochrome | Visual effect is improved |
| Portability (in weight) | 53 grams | 98 grams | Easy to carry |

Comparative data of a stethoscope of the fifth embodiment of the present disclosure with the KS-520B type of stethoscope are shown below.

| Type of stethoscope with two sound collecting surfaces | The inventive stethoscope | KS-520B | Data comparison result |
|---|---|---|---|
| Structure | Both of an upper head body and a lower head body are made of a combination of high density material and low density material | Made of only high density material | |
| Name of high density material | Stainless steel (type 304) | Stainless steel(type 304) | |
| Material consumption and cost | 33.3 grams × CNY 0.035 per gram = CNY 1.16 | 103 grams × CNY 0.035 per gram = CNY 3.6 | |

-continued

| Type of stethoscope with two sound collecting surfaces | The inventive stethoscope | KS-520B | Data comparison result |
|---|---|---|---|
| Name of low-density material | Polyformaldehyde (POM) | | |
| Material consumption and cost | 23.5 grams × CNY 0.025 per gram = CNY 0.58 | | |
| Cutting tool consumption | CNY 2.33 | CNY 2.94 | |
| Machining time and cost | 276 second × CNY 0.011 per second = CNY 3.03 | 401 second × CNY 0.011 per second = CNY 4.41 | Machining time is saved by 32% |
| Total cost | CNY 7.1 | CNY 10.95 | Total cost is save by 36% |
| Sound conducting performance test (where a sound is collected by a sound collecting chamber of the stethoscope) | Sound source: 114 dB 1000 HZ Measured value 115.7 dB Sound source: 114 dB 500 HZ Measured value: 108.3 dB | Sound source: 114 dB 1000 HZ Measured value 112.3 dB Sound source: 114 dB 500 HZ Measured value: 104.4 dB | Sound conducting performance has no significant change |
| External noise resistance performance test (where a sound is collected by a back of the stethoscope) | Sound source: 114 dB 1000 HZ Measured value: 33.1 dB Sound source: 114 dB 500 HZ Measured value: 27.4 dB | Sound source: 114 dB 1000 HZ Measured value: 43.6 dB Sound source: 114 dB 500 HZ Measured value: 35.9 dB | External noise resistance is improved by 24% to 25% |
| Aesthetics (two colors mixed) | With two colors mixed | Monochrome | Visual effect is improved |
| Portability (in weight) | 56 grams | 108 grams | Easy to carry |

Comparative data of a stethoscope of the fifth embodiment of the present disclosure with the KS-520C type of stethoscope are shown below.

| Type of stethoscope with two sound collecting surfaces | The inventive stethoscope | KS-520C | Data comparison result |
|---|---|---|---|
| Structure | Both of an upper head body and a lower head body are made of a combination of high density material and low density material | Made of only high density material | |
| Name of high density material | Stainless steel (type 304) | Stainless steel(type 304) | |
| Material consumption and cost | 31.5 grams × CNY 0.035 per gram = CNY 1.1 | 106 grams × CNY 0.035 per gram = CNY 3.71 | |
| Name of low-density material | Polyformaldehyde (POM) | | |
| Material consumption and cost | 22.5 grams × CNY 0.025 per gram = CNY 0.56 | | |
| Cutting tool consumption | CNY 2.5 | CNY 2.96 | |
| Machining time and cost | 290 second × CNY 0.011 per second = CNY 3.19 | 388 second × CNY 0.011 per second = CNY 4.26 | Machining time is saved by 26% |
| Total cost | CNY 7.35 | CNY 10.93 | Total cost is save by 33% |
| Sound conducting performance test (where a sound is collected by a sound collecting chamber of the stethoscope) | Sound source: 114 dB 1000 HZ Measured value: 120.3 dB Sound source: 114 dB 500 HZ Measured value: 111 dB | Sound source: 114 dB 1000 HZ Measured value: 125 dB Sound source: 114 dB 500 HZ Measured value: 108.6 dB | Sound conducting performance has no significant change |
| External noise resistance performance test | Sound source: 114 dB 1000 HZ Measured value: 31.4 dB | Sound source: 114 dB 1000 HZ Measured value: 43.3 dB | External noise resistance is |

| Type of stethoscope with two sound collecting surfaces | The inventive stethoscope | KS-520C | Data comparison result |
|---|---|---|---|
| (where a sound is collected by a back of the stethoscope) | Sound source: 114 dB 500 HZ Measured value: 28.5 dB | Sound source: 114 dB 500 HZ Measured value: 37.8 dB | improved by 25% to 28% |
| Aesthetics (two colors mixed) | With two colors mixed | Monochrome | Visual effect is improved |
| Portability (in weight) | 50 grams | 92 grams | Easy to carry |

It can be known from the above comparative data that time for manufacturing the inventive stethoscope is saved by about 30%, a cost for manufacturing the inventive stethoscope is reduced by about 30%, the external noise resistance of the inventive stethoscope is improved by about 20%, a weight of the inventive stethoscope is reduced by about one third, without significant change to the sound conducting performance, and the stethoscope is easy to carry and has a good appearance.

What is claimed is:

1. A stethoscope head, comprising:
a head body and a sound guiding conduit formed in the head body, wherein the sound guiding conduit comprises one or more one sound collecting surfaces that is concave;
the sound guiding conduit further comprising:
a sound guiding pore and
a lateral sound guiding aperture;
wherein the one or more sound collecting surfaces, the sound guiding pore and the lateral sound guiding aperture being intercommunicated with each other;
wherein a sound guiding layer is an inner lining that conforms to the one or more sound collecting surfaces and is made of a material of a first density;
wherein at least one sound collecting surface is made of material of a second density; and
wherein the first density is larger than the second density.

2. The stethoscope head of claim 1, wherein, a density of a sound guiding layer in the sound guiding pore is larger than the second density, and the density of the sound guiding layer in the sound guiding pore is different from the density of the sound guiding layer on the sound collecting surface.

3. The stethoscope head of claim 1, wherein, the head body is assembled and comprises an upper head body and a lower head body which are connected with each other, the one or more sound collecting surfaces comprise an upper sound collecting surface disposed on the upper head body and a lower sound collecting surface disposed on the lower head body, the upper sound collecting surface is communicated with the lower sound collecting surface through the sound guiding pore, the sound guiding pore is communicated with lateral sound guiding aperture.

4. The stethoscope head of claim 3, wherein, the upper sound collecting surface is made of material of the first density, the lower sound collecting surface is made of the material of the second density.

5. The stethoscope head of claim 3, wherein, the lower sound collecting surface is made of material of the first density, the upper sound collecting surface is made of the material of the second density.

6. The stethoscope head of claim 3, wherein, both of the lower sound collecting surface and the upper sound collecting surface are made of the material of the second density.

7. The stethoscope head of claim 1, wherein, the head body is integrated and made of the material of the second density.

8. The stethoscope head of claim 2, wherein, the head body is assembled and comprises an upper head body and a lower head body which are connected with each other, the one or more sound collecting surfaces comprise an upper sound collecting surface disposed on the upper head body and a lower sound collecting surface disposed on the lower head body, the upper sound collecting surface is communicated with the lower sound collecting surface through the sound guiding pore, the sound guiding pore is communicated with lateral sound guiding aperture.

9. The stethoscope head of claim 2, wherein, the head body is integrated and made of the material of the second density.

10. The stethoscope head of claim 1, wherein, a density of a sound guiding layer in the sound guiding pore is larger than the second density, and the density of the sound guiding layer in the sound guiding pore is the same as the density of the sound guiding layer on the sound collecting surface.

11. The stethoscope head of claim 1, wherein, the head body are formed by injection molding.

12. The stethoscope head of claim 1, wherein, a sound guiding layer on the sound guiding pore is interference fitted or thread fitted with the sound guiding pore.

13. A method for reducing a weight of a stethoscope head, wherein the stethoscope head comprises:
a head body and a sound guiding conduit formed in the head body, wherein the sound guiding conduit comprises one or more one sound collecting surfaces that is concave;
the sound guiding conduit further comprises:
a sound guiding pore and
a lateral sound guiding aperture;
wherein the one or more sound collecting surfaces, the sound guiding pore and the lateral sound guiding aperture are intercommunicated with each other;
wherein a sound guiding layer is an inner lining that conforms to the one or more sound collecting surfaces;
wherein the method comprises:
providing a material of a first density, wherein at least the sound guiding layer on each of the sound collecting surfaces is made of the material of the first density so as to ensure sound conducting quality of the stethoscope head;
providing a material of a second density, wherein at least one sound collecting surface is made of the material of the second density, wherein the second density is less than the first density.

14. The method of claim 13, wherein, a sound guiding layer in the sound guiding pore is made of material of a third density, the second density is less than the third density, and the third density is different from the first density.

* * * * *